(12) United States Patent
Finch et al.

(10) Patent No.: US 12,403,324 B2
(45) Date of Patent: Sep. 2, 2025

(54) WEARABLE MEDICAL DEVICE (WMD) IMPLEMENTING ADAPTIVE TECHNIQUES TO SAVE POWER

(71) Applicant: West Affum Holdings DAC, Dublin (IE)

(72) Inventors: David P. Finch, Bothell, WA (US); Erick M. Roane, Bellevue, WA (US); Kenneth F. Cowan, Kirkland, WA (US); Derek J. Valleroy, Seattle, WA (US); Gregory T. Kavounas, Bellevue, WA (US)

(73) Assignee: West Affum Holdings DAC, Dublin (IE)

( * ) Notice: Subject to any disclaimer, the term of this patent is extended or adjusted under 35 U.S.C. 154(b) by 323 days.

(21) Appl. No.: 17/682,245

(22) Filed: Feb. 28, 2022

(65) Prior Publication Data

US 2022/0296909 A1    Sep. 22, 2022

Related U.S. Application Data

(63) Continuation of application No. 16/453,488, filed on Jun. 26, 2019, now Pat. No. 11,260,238.

(51) Int. Cl.
*A61B 5/364* (2021.01)
*A61B 5/024* (2006.01)
(Continued)

(52) U.S. Cl.
CPC ............ *A61N 1/3987* (2013.01); *A61B 5/024* (2013.01); *A61B 5/282* (2021.01); *A61B 5/308* (2021.01);
(Continued)

(58) Field of Classification Search
CPC ............................ A61N 1/3987; A61B 5/364
(Continued)

(56) References Cited

U.S. PATENT DOCUMENTS

| 3,724,455 A | 4/1973 | Unger |
| 4,583,524 A | 4/1986 | Hutchins |

(Continued)

FOREIGN PATENT DOCUMENTS

WO    9839061 A2    9/1998

OTHER PUBLICATIONS

Heartstart MRx and XL AED Algorithm—Application Note, Jul. 2001, Edition 2 Philips Healthcare, USA.
(Continued)

*Primary Examiner* — Nicole F Johnson
(74) *Attorney, Agent, or Firm* — POLSINELLI PC

(57) ABSTRACT

A wearable cardioverter defibrillator (WCD) comprises a plurality of electrocardiography (ECG) electrodes and a plurality of defibrillator electrodes to contact the patient's skin when the WCD is delivering therapy to the patient, a preamplifier coupled to the ECG electrodes to obtain ECG data from the patient. a processor to receive the ECG data from the preamplifier, and a high voltage subsystem to provide a defibrillation voltage to the patient through the plurality of defibrillator electrodes in response to a shock signal received from the processor. In a first power mode of a range of power modes the preamplifier is configured to perform low-fidelity ECG acquisition and the processor is configured to perform simple arrythmia detection analysis, and in a second mode of the range of power modes the preamplifier is configured to perform high-fidelity ECG acquisition and the processor is configured to perform complex arrythmia detection analysis.

20 Claims, 7 Drawing Sheets

(51) Int. Cl.
    *A61B 5/282*      (2021.01)
    *A61B 5/308*      (2021.01)
    *A61N 1/04*      (2006.01)
    *A61N 1/39*      (2006.01)

(52) U.S. Cl.
    CPC ............ *A61B 5/364* (2021.01); *A61N 1/0484* (2013.01); *A61N 1/3993* (2013.01)

(58) Field of Classification Search
    USPC .......................................................... 607/7
    See application file for complete search history.

(56) References Cited

U.S. PATENT DOCUMENTS

| | | |
|---|---|---|
| 4,619,265 A | 10/1986 | Morgan et al. |
| 4,928,690 A | 5/1990 | Heilman et al. |
| 4,955,381 A | 9/1990 | Way et al. |
| 5,078,134 A | 1/1992 | Heilman et al. |
| 5,228,449 A | 7/1993 | Christ et al. |
| 5,348,008 A | 9/1994 | Bornn et al. |
| 5,353,793 A | 10/1994 | Bornn |
| RE34,800 E | 11/1994 | Hutchins |
| 5,394,892 A | 3/1995 | Kenny et al. |
| 5,405,362 A | 4/1995 | Kramer et al. |
| 5,474,574 A | 12/1995 | Payne et al. |
| 5,662,690 A | 9/1997 | Cole et al. |
| 5,782,878 A | 7/1998 | Morgan et al. |
| 5,792,204 A | 8/1998 | Snell |
| 5,902,249 A | 5/1999 | Lyster |
| 5,913,685 A | 6/1999 | Hutchins |
| 5,944,669 A | 8/1999 | Kaib |
| 6,047,203 A | 4/2000 | Sackner et al. |
| 6,065,154 A | 5/2000 | Hulings et al. |
| 6,108,197 A | 8/2000 | Janik |
| 6,148,233 A | 11/2000 | Owen et al. |
| 6,201,992 B1 | 3/2001 | Freeman |
| 6,263,238 B1 | 7/2001 | Brewer et al. |
| 6,287,328 B1 | 9/2001 | Snyder et al. |
| 6,304,780 B1 | 10/2001 | Owen et al. |
| 6,319,011 B1 | 11/2001 | Motti et al. |
| 6,334,070 B1 | 12/2001 | Nova et al. |
| 6,356,785 B1 | 3/2002 | Snyder et al. |
| 6,427,083 B1 | 7/2002 | Owen et al. |
| 6,529,875 B1 | 3/2003 | Nakajima et al. |
| 6,546,285 B1 | 4/2003 | Owen et al. |
| 6,671,545 B2 | 12/2003 | Fincke |
| 6,681,003 B2 | 1/2004 | Linder et al. |
| 6,762,917 B1 | 7/2004 | Verbiest et al. |
| 7,065,401 B2 | 6/2006 | Worden |
| 7,559,902 B2 | 7/2009 | Ting et al. |
| 7,865,238 B2 | 1/2011 | Brink |
| 7,870,761 B2 | 1/2011 | Valentine et al. |
| 7,974,689 B2 | 7/2011 | Volpe et al. |
| 8,135,462 B2 | 3/2012 | Owen et al. |
| 8,140,154 B2 | 3/2012 | Donnelly et al. |
| 8,369,944 B2 | 2/2013 | Macho et al. |
| 8,548,557 B2 | 10/2013 | Garstka et al. |
| 8,615,295 B2 | 12/2013 | Savage et al. |
| 8,644,925 B2 | 2/2014 | Volpe et al. |
| 8,897,860 B2 | 11/2014 | Volpe et al. |
| 8,904,213 B2 | 12/2014 | Chan et al. |
| 8,904,214 B2 | 12/2014 | Volpe et al. |
| 8,965,500 B2 | 2/2015 | Macho et al. |
| 9,008,801 B2 | 4/2015 | Kaib et al. |
| 9,089,685 B2 | 7/2015 | Sullivan et al. |
| 9,131,901 B2 | 9/2015 | Volpe et al. |
| 9,132,267 B2 | 9/2015 | Kaib |
| 9,408,548 B2 | 8/2016 | Volpe et al. |
| 9,454,219 B2 | 9/2016 | Volpe et al. |
| 9,592,403 B2 | 3/2017 | Sullivan |
| 2003/0158593 A1 | 8/2003 | Heilman et al. |
| 2005/0107833 A1 | 5/2005 | Freeman et al. |
| 2005/0107834 A1 | 5/2005 | Freeman et al. |
| 2008/0312709 A1 | 12/2008 | Volpe et al. |
| 2009/0005827 A1 | 1/2009 | Weintraub et al. |
| 2010/0007413 A1 | 1/2010 | Herleikson et al. |
| 2010/0298899 A1 | 11/2010 | Donnelly et al. |
| 2011/0022105 A9 | 1/2011 | Owen et al. |
| 2011/0288604 A1 | 11/2011 | Kaib et al. |
| 2011/0288605 A1 | 11/2011 | Kaib et al. |
| 2012/0112903 A1 | 5/2012 | Kaib et al. |
| 2012/0144551 A1 | 6/2012 | Guldalian |
| 2012/0150008 A1 | 6/2012 | Kaib et al. |
| 2012/0158075 A1 | 6/2012 | Kaib et al. |
| 2012/0265265 A1 | 10/2012 | Razavi et al. |
| 2012/0283794 A1 | 11/2012 | Kaib et al. |
| 2012/0293323 A1 | 11/2012 | Kaib et al. |
| 2012/0302860 A1 | 11/2012 | Volpe et al. |
| 2012/0310315 A1 | 12/2012 | Savage et al. |
| 2013/0085538 A1 | 4/2013 | Volpe et al. |
| 2013/0231711 A1 | 9/2013 | Kaib |
| 2013/0245388 A1 | 9/2013 | Rafferty et al. |
| 2013/0274565 A1 | 10/2013 | Langer et al. |
| 2013/0317852 A1 | 11/2013 | Worrell et al. |
| 2013/0325078 A1 | 12/2013 | Whiting et al. |
| 2014/0025131 A1 | 1/2014 | Sullivan et al. |
| 2014/0070957 A1 | 3/2014 | Longinotti-Buitoni et al. |
| 2014/0163663 A1 | 6/2014 | Poddar et al. |
| 2014/0324112 A1 | 10/2014 | Macho et al. |
| 2014/0378812 A1 | 12/2014 | Saroka et al. |
| 2015/0039053 A1 | 2/2015 | Kaib et al. |
| 2015/0305642 A1 | 10/2015 | Reinke et al. |
| 2015/0328472 A1 | 11/2015 | Sullivan et al. |
| 2016/0004831 A1 | 1/2016 | Carlson et al. |
| 2016/0029905 A1* | 2/2016 | Kovacs .............. A61B 5/02055 600/301 |
| 2016/0082277 A1 | 3/2016 | Foshee, Jr. et al. |
| 2016/0253471 A1* | 9/2016 | Volpe ..................... G16H 40/40 607/5 |
| 2016/0296114 A1* | 10/2016 | Finch ....................... A61N 1/08 |
| 2017/0003356 A1* | 1/2017 | Kaib .................... A61N 1/3708 |
| 2017/0156617 A1* | 6/2017 | Allavatam ............. A61B 5/349 |
| 2018/0272145 A1 | 9/2018 | Medema et al. |

OTHER PUBLICATIONS

Klein, H. U., Goldenberg I., & Moss, A. J., Risk Stratification for Implantable Cardioverter Defibrillator Therapy: The Role of the Wearable Cardioverter-Defibrillator, Clinical update, European Heart Journal, May 31, 2013, pp. 1-14, doi:10.1093/eurheartj/eht167, European Society of Cardiology.

Lifecor LifeVest System Model WCD 3100 Operator's Manual, 2006, PN 20B0040 Rev FI, Zoll Lifecor Corporation, Pittsburgh, PA.

LifeVest Model 4000 Patient Manual, Zoll, 2009, PN 20B0047 Rev B.

Pagan-Carlo, et al., "Encircling Overlapping Multipulse Shock Waveforms for Transthoracic Defibrillation," JACC Journals, Dec. 1998, vol. 32 Issue 7, p. 2065-2071.

The LifeVest Network/Patient Data Management System, Zoll, 2015, 2000503 Rev A.

* cited by examiner

WEARABLE MEDICAL DEVICE (WMD) IMPLEMENTING ADAPTIVE TECHNIQUES TO SAVE POWER

CROSS-REFERENCE TO RELATED APPLICATIONS

The present application is a continuation of U.S. application Ser. No. 16/453,488 filed on Jun. 26, 2019 (C00003539.USU2), now U.S. Pat. No. 11,260,238, which in turn claims the benefit of U.S. Provisional Application No. 62/662,916 (C00003539.USP1) filed on Apr. 26, 2018. Said application Ser. No. 16/453,488, said Application No. 62/662,916, and U.S. Pat. No. US 11,260,238 are hereby incorporated herein by reference in their entireties for all purposes.

BACKGROUND

When people suffer from some types of heart arrhythmias, the result may be that blood flow to various parts of the body is reduced. Some arrhythmias may even result in a Sudden Cardiac Arrest (SCA). SCA can lead to death very quickly, for example within 10 minutes, unless treated in the interim.

Some people have an increased risk of SCA. Such people include patients who have had a heart attack, or a prior SCA episode. A frequent recommendation for these people is to receive an Implantable Cardioverter Defibrillator (ICD). The ICD is surgically implanted in the chest, and continuously monitors the patient's electrocardiogram (ECG). If certain types of heart arrhythmias are detected, then the ICD delivers an electric shock through the heart.

As a further precaution, people who have been identified to have an increased risk of an SCA are sometimes given a Wearable Cardioverter Defibrillator (WCD) system, to wear until the time that their ICD is implanted. Early versions of such systems were called wearable cardiac defibrillator systems. A WCD system typically includes a harness, vest, belt, or other garment that the patient is to wear. The WCD system further includes electronic components, such as a defibrillator and electrodes, coupled to the harness, vest, or another garment. When the patient wears the WCD system, the electrodes may make good electrical contact with the patient's skin, and therefore can help sense the patient's ECG. If a shockable heart arrhythmia is detected from the ECG, then the defibrillator delivers an appropriate electric shock through the patient's body, and thus through the heart. This may restart the patient's heart and thus save their life.

Battery-powered, wearable medical devices (WMDs) are systems that can be worn by ambulatory patients. These WMDs often have tasks or operations that need to be performed continuously and therefore that need to be power-efficient. For example, acquisition of a patient's ECG and preliminary analysis of the ECG for an arrhythmia is an operation that should be done continuously for a WMD that is a Wearable Cardioverter Defibrillator (WCD) system. When different events happen, such as inputs on a User Interface, receipt of external communication, or preliminary signs of an arrhythmia, the WMD should adapt and bring to bear more processing power and/or different capabilities to address the event.

DESCRIPTION OF THE DRAWING FIGURES

Claimed subject matter is particularly pointed out and distinctly claimed in the concluding portion of the specification. However, such subject matter may be understood by reference to the following detailed description when read with the accompanying drawings in which:

Figure 1:
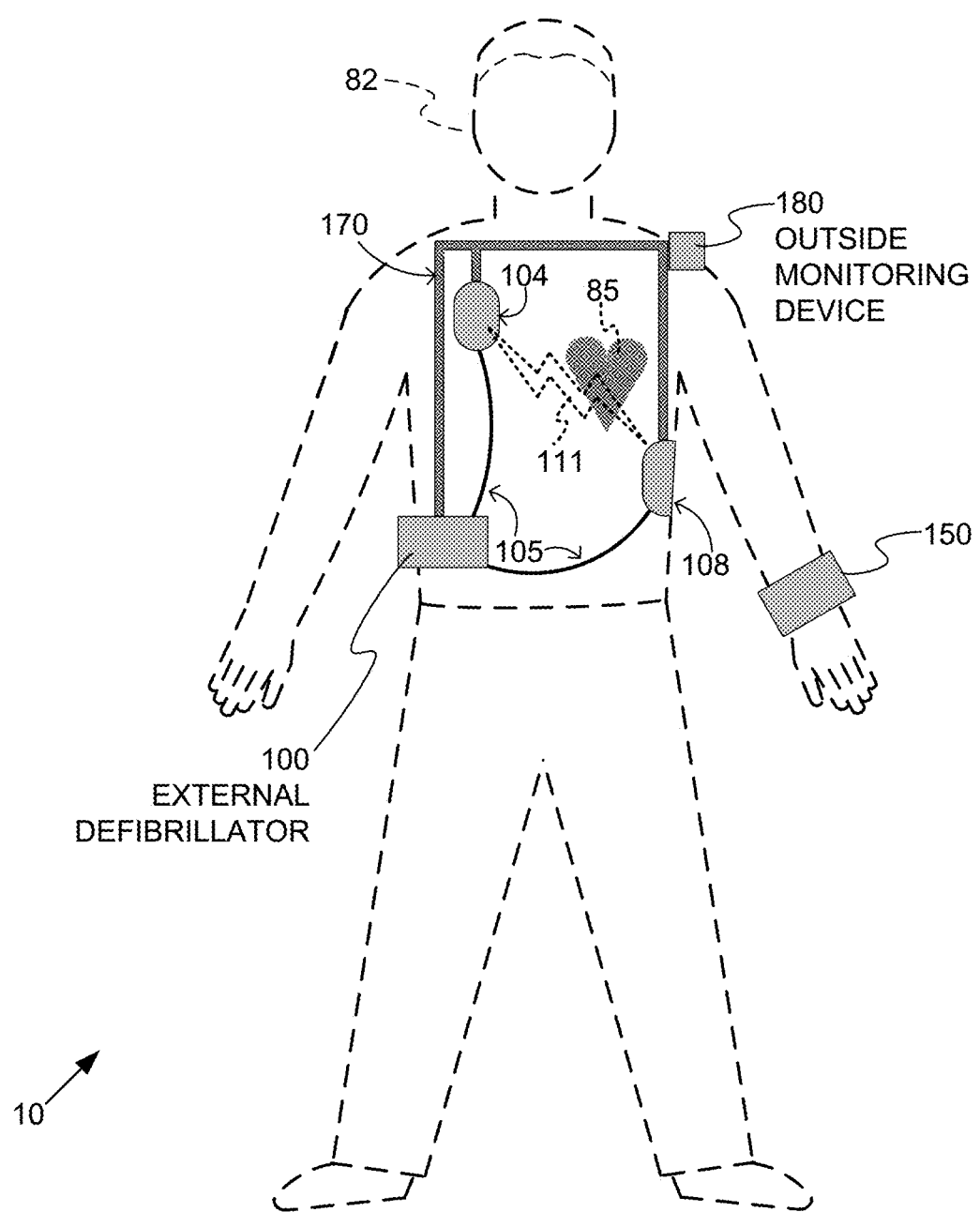
FIG. 1 is a diagram of components of a wearable medical device (WMD) that can comprise a sample wearable cardioverter defibrillator (WCD) system or another form factor of a battery powered WMD such as a wrist worn WMD in accordance with one or more embodiments.

It will be appreciated that for simplicity and/or clarity of illustration, elements illustrated in the figures have not necessarily been drawn to scale. For example, the dimensions of some of the elements may be exaggerated relative to other elements for clarity. Further, if considered appropriate, reference numerals have been repeated among the figures to indicate corresponding and/or analogous elements.

DETAILED DESCRIPTION

In the following detailed description, numerous specific details are set forth to provide a thorough understanding of claimed subject matter. It will, however, be understood by those skilled in the art that claimed subject matter may be practiced without these specific details. In other instances, well-known methods, procedures, components and/or circuits have not been described in detail.

In the following description and/or claims, the terms coupled and/or connected, along with their derivatives, may be used. In particular embodiments, connected may be used to indicate that two or more elements are in direct physical and/or electrical contact with each other. Coupled may mean that two or more elements are in direct physical and/or electrical contact. Coupled, however, may also mean that two or more elements may not be in direct contact with each other, but yet may still cooperate and/or interact with each other. For example, "coupled" may mean that two or more elements do not contact each other but are indirectly joined together via another element or intermediate elements. Finally, the terms "on," "overlying," and "over" may be used in the following description and claims. "On," "overlying," and "over" may be used to indicate that two or more elements are in direct physical contact with each other. It should be noted, however, that "over" may also mean that two or more elements are not in direct contact with each other. For example, "over" may mean that one element is above another element but not contact each other and may have another element or elements in between the two elements. Furthermore, the term "and/or" may mean "and", it may mean "or", it may mean "exclusive-or", it may mean "one", it may mean "some, but not all", it may mean "neither", and/or it may mean "both", although the scope of claimed subject matter is not limited in this respect. In the following description and/or claims, the terms "comprise" and "include," along with their derivatives, may be used and are intended as synonyms for each other.

FIG. 1 is a diagram of components of a wearable medical device (WMD) that can comprise a sample wearable cardioverter defibrillator (WCD) system or another form factor of a battery powered WMD such as a wrist worn WMD in accordance with one or more embodiments. A wearable cardioverter defibrillator (WCD) system 10 according to embodiments may protect an ambulatory patient by electrically restarting his or her heart if needed. Such a WCD system 10 may have a number of components. These components can be provided separately as modules that can be interconnected, or can be combined with other components, and so on.

In one or more embodiments, WCD system 10 can comprise one or more battery-operated, wearable medical device (WMD) systems, that use hardware and/or software components that can dynamically provide different levels of performance and/or capability at correspondingly-different power consumption levels, for efficient, flexible control over the power consumption of a battery-operated, wearable medical device. These techniques or methods allow the WMD systems to meet a broad range of required capability, on-the-fly, while consuming the least amount of power overall. Such a WMD system may thus alternate between a higher-performance monitoring state and a lower-performance monitoring state, and also other monitoring states at operating points in between. These adaptive methods can provide significant power saving for medical devices without requiring special-purpose processors, special power-saving modes, or complicated software schemes. In some examples, WCD system 10 may be considered a wearable medical device (WMD) that is battery powered and can operate with one or more other WMDs such as a small form factor WMD 150 that also can be battery operated and worn on the body of a patient. In some examples, the term WMD can refer to a single device, a system comprising one or more subsystems, a system comprising one or more devices, or a system that comprises one or more devices and/or one or more subsystems, and the scope of the disclosed subject matter is not limited in these respects.

FIG. 1 depicts a patient 82. Patient 82 may also be referred to as a person and/or wearer, since the patient is wearing components of the WCD system 10. Patient 82 is ambulatory, which means that, while wearing the wearable portion of the WCD system 10, patient 82 can walk around and is not necessarily bed-ridden. While patient 82 may be considered to be also a "user" of the WCD system 10, this is not a requirement. For instance, a user of the wearable cardioverter defibrillator (WCD) may also be a clinician such as a doctor, nurse, emergency medical technician (EMT) or other similarly tasked individual or group of individuals. In some cases, a user may even be a bystander. The particular context of these and other related terms within this description should be interpreted accordingly.

A WCD system 10 according to embodiments can be configured to defibrillate the patient 82 who is wearing the designated parts the WCD system 10. Defibrillating can be by the WCD system 10 delivering an electrical charge to the patient's body in the form of an electric shock. The electric shock can be delivered in one or more pulses.

FIG. 1 also depicts components of a WCD system 10 made according to embodiments. One such component is a support structure 170, or garment, that is wearable by ambulatory patient 82. Accordingly, support structure 170 is configured to be worn by ambulatory patient 82 for at least several hours per day, and for at least several days, even a few months. It will be understood that support structure 170 is shown only generically in FIG. 1, and in fact partly conceptually. FIG. 1 is provided merely to illustrate concepts about support structure 170, and is not to be construed as limiting how support structure 170 is implemented, or how it is worn.

Support structure 170 can be implemented in many different ways. For example, it can be implemented in a single component or a combination of multiple components. In embodiments, support structure 170 could include a vest, a half-vest, a garment, etc. In such embodiments such items can be worn similarly to analogous articles of clothing. In embodiments, support structure 170 could include a harness, one or more belts or straps, etc. In such embodiments, such items can be worn by the patient around the torso, hips, over the shoulder, etc. In embodiments, support structure 170 can include a container or housing, which can even be waterproof. In such embodiments, the support structure can be worn by being attached to the patient's body by adhesive material, for example as shown and described in U.S. Pat. No. 8,024,037 which is incorporated herein by reference in its entirety. Support structure 170 can even be implemented as described for the support structure of U.S. application Ser. No. 15/120,655, published as US 2017/0056682 A1, which is incorporated herein by reference in its entirety. In such embodiments, the person skilled in the art will recognize that additional components of the WCD system 10 can be in the housing of a support structure instead of being attached externally to the support structure, for example as described in the US 2017/0056682 A1 document. There can be other examples.

FIG. 1 shows a sample external defibrillator 100. As described in more detail later in this document, some aspects of external defibrillator 100 include a housing and an energy storage module within the housing. As such, in the context of a WCD system 10, defibrillator 100 is sometimes called a main electronics module or a monitor. The energy storage module can be configured to store an electrical charge. Other components can cause at least some of the stored electrical charge to be discharged via electrodes through the patient to deliver one or more defibrillation shocks through the patient 82.

FIG. 1 also shows sample defibrillation electrodes 104 and/or 108, which are coupled to external defibrillator 100 via electrode leads 105. Defibrillation electrodes 104 and/or 108 can be configured to be worn by patient 82 in several ways. For instance, defibrillator 100 and defibrillation electrodes 104 and/or 108 can be coupled to support structure 170, directly or indirectly. In other words, support structure 170 can be configured to be worn by ambulatory patient 82 to maintain at least one of electrodes 104 and/or 108 on the body of ambulatory patient 82, while patient 82 is moving around, etc. The electrode can be thus maintained on the body by being attached to the skin of patient 82, simply pressed against the skin directly or through garments, etc. In some embodiments the electrode is not necessarily pressed against the skin, but becomes biased that way upon sensing a condition that could merit intervention by the WCD system 10. In addition, many of the components of defibrillator 100 can be considered coupled to support structure 170 directly, or indirectly via at least one of defibrillation electrodes 104 and/or 108.

When defibrillation electrodes 104 and/or 108 make good electrical contact with the body of patient 82, defibrillator 100 can administer, via electrodes 104 and/or 108, a brief, strong electric pulse 111 through the body. Pulse 111 is also known as shock, defibrillation shock, therapy, electrotherapy, therapy shock, etc. Pulse 111 is intended to go through and restart heart 85, in an effort to save the life of patient 82. Pulse 111 can further include one or more pacing pulses of lesser magnitude to simply pace heart 85 if needed, and so on.

A typical defibrillator decides whether to defibrillate or not based on an ECG signal of the patient. External defibrillator 100, however, may initiate defibrillation, or hold-off defibrillation, based on a variety of inputs, with the ECG signal merely being one of these inputs.

A WCD system 10 according to embodiments can obtain data from patient 82. For collecting such data, the WCD system 10 may optionally include at least an outside monitoring device 180. Device 180 is called an "outside" device because it could be provided as a standalone device, for example not within the housing of defibrillator 100. Device 180 can be configured to sense or monitor at least one local parameter. A local parameter can be a parameter of patient 82, or a parameter of the WCD system 10, or a parameter of the environment, as will be described later in this document. In some embodiments, outside monitoring device 180 can comprise a hub or similar device through which connections and/or leads may be made of the various components of the WCD system 100. For example, at least some of the leads of external defibrillator 100 may be connected to and/or routed through the outside monitoring device 180 including, for example, one or more ECG leads, a right-leg drive (RLD) lead, leads connected to the defibrillation electrodes 104 and/or 108, and so on. In some embodiments, outside monitoring device 180 can include a controller or processor that is used to implement at least a portion of the shock/no-shock algorithm to determine whether a shock should or should not be applied to the patient 82, although the scope of the disclosed subject matter is not limited in this respect.

For some of these parameters, device 180 may include one or more sensors or transducers. Each one of such sensors can be configured to sense a parameter of patient 82, and to render an input responsive to the sensed parameter. In some embodiments the input is quantitative, such as values of a sensed parameter. In other embodiments the input is qualitative, such as informing whether or not a threshold is crossed, and so on. Sometimes these inputs about patient 82 are also called physiological inputs and patient inputs. In embodiments, a sensor can be construed more broadly, as encompassing many individual sensors.

Optionally, device 180 is physically coupled to support structure 170. In addition, device 180 may be communicatively coupled with other components that are coupled to support structure 170. Such communication can be implemented by a communication module, as will be deemed applicable by a person skilled in the art in view of this description.

In embodiments, one or more of the components of the shown WCD system 10 may be customized for patient 82. This customization may include a number of aspects. For instance, support structure 170 can be fitted to the body of patient 82. For another instance, baseline physiological parameters of patient 82 can be measured, such as the heart rate of patient 82 while resting, while walking, motion detector outputs while walking, etc. The measured values of such baseline physiological parameters can be used to customize the WCD system 10, in order to make its diagnoses more accurate, since patients' bodies differ from one another. Of course, such parameter values can be stored in a memory of the WCD system 10, and so on. Moreover, a programming interface can be made according to embodiments, which receives such measured values of baseline physiological parameters. Such a programming interface may input automatically in the WCD system 10 these, along with other data.

In one or more embodiments, WCD system 10 may include a small form factor wearable medical device (WMD) 150 that is capable of collecting one or more of the patient parameters collected by WCD system 10. In some examples, the small form factor WMD 150 can comprise a non-invasive blood pressure monitor that is capable of obtaining a blood pressure reading of the patient 82 without insertion of catheter into a patient's blood vessel. In some embodiments, the small form factor WMD 150 comprises a cuff-less blood-pressure monitor 150 in that it is capable of obtaining a blood pressure reading without using a conventional cuff device placed around the patient's arm that is inflated and deflated to obtain the measurement. Furthermore, in some examples the small form factor WMD 150 can obtain frequent blood pressure measurements while the patient 82 is wearing the monitor through the day and/or during the night when the patient 82 is sleeping. It should be noted that a blood pressure monitor is merely one example of the small form factor WMD 150, and in general small form factor WMD 150 can comprise other types of patient parameter collecting devices including a heart rate monitor or a peripheral capillary oxygen saturation (SpO2) monitor, and the scope of the disclosure is not limited in this respect.

In some examples, the small form factor WMD 150 may be provided in various types of form factors to be placed on the patient's body at various locations and/or to integrate with WCD system 10 in various ways. For example, in some embodiments, the small form factor WMD 150 may be worn on the wrist of the patient 82 or various other locations on the patient 82 such as on the arm, leg, ankle, chest, or back of the patient 82 depending on the provided form factor and/or technology utilized by the small form factor WMD 150 to obtain a blood pressure reading.

In some embodiments, the small form factor WMD 150 may be incorporated into an external device or accessory such as a smartphone. Such devices may come in various other form factors such as a patch, watch, earring, eye glasses, ankle bracelet, and so on, wherein the small form factor WMD 150 can be unobtrusive and in location in which the patient's vasculature may be near the skin so that an optical sensor or other sensor of the small form factor WMD 150 can obtain good readings.

In one or more embodiments, the small form factor WMD 150 can include or otherwise comprise an optical pulse oximetry sensor and/or a methemoglobin sensor wherein optical sensor functionality can be implemented using a pulse oximetry or methemoglobin sensor. In other embodiments, the small form factor WMD 150 can be coupled with one or more of the ECG electrodes of the WCD system 10. Such a sensor can be an optical sensor as described above, or an electro-mechanical sensor such as described in "*A CMOS-based Tactile Sensor for Continuous Blood Pressure Monitoring*", Kirstein, Sedivy, et al., Proceedings of the Design, Automation and Test in Europe Conference and Exhibition, 1530-1591/05 (Mar. 2005) which is incorporated herein by reference in its entirety.

In other embodiments, the small form factor WMD 150 can be adapted for use in proposed adhesive type defibrillators as disclosed in U.S. Pat. No. 8,024,037. For example, the small form factor WMD 150 can be disposed in one of the adhesive modules as shown in the '037 patent, or in an "appendage" or "flap" that extends from the module so that the NIBP monitor 150 is positioned on an appropriate location on the patient. Embodiments of a the small form factor WMD 150 sensor can include a wireless communication interface such as BLUETOOTH, near-field communication (NFC), Wi-Fi DIRECT, ZIGBEE, and so on, to transmit the patient parameter data to a module of the WCD system 10, to a personal communication device of the WCD system 10 for example as disclosed in U.S. Pat. No. 8,838,235, or to another remote device. Said U.S. Pat. No. 8,838,235 is incorporated herein by reference in its entirety. In some embodiments, a wired communication link can be used instead of a wireless communication link. For example, the small form factor WMD 150 can be implemented in an electrode that can be configured so that the patient parameter data is transmitted on a wire bundled with the wire or wires of the electrode sensors or multiplexed on the same wire as the electrode data, and so on. In one or more embodiments, the small form factor WMD 150 can include its own power control module to control its operational power either alone or in conjunction with the power control of WCD system 10 as will be discussed in further detail, below.

Figure 2:
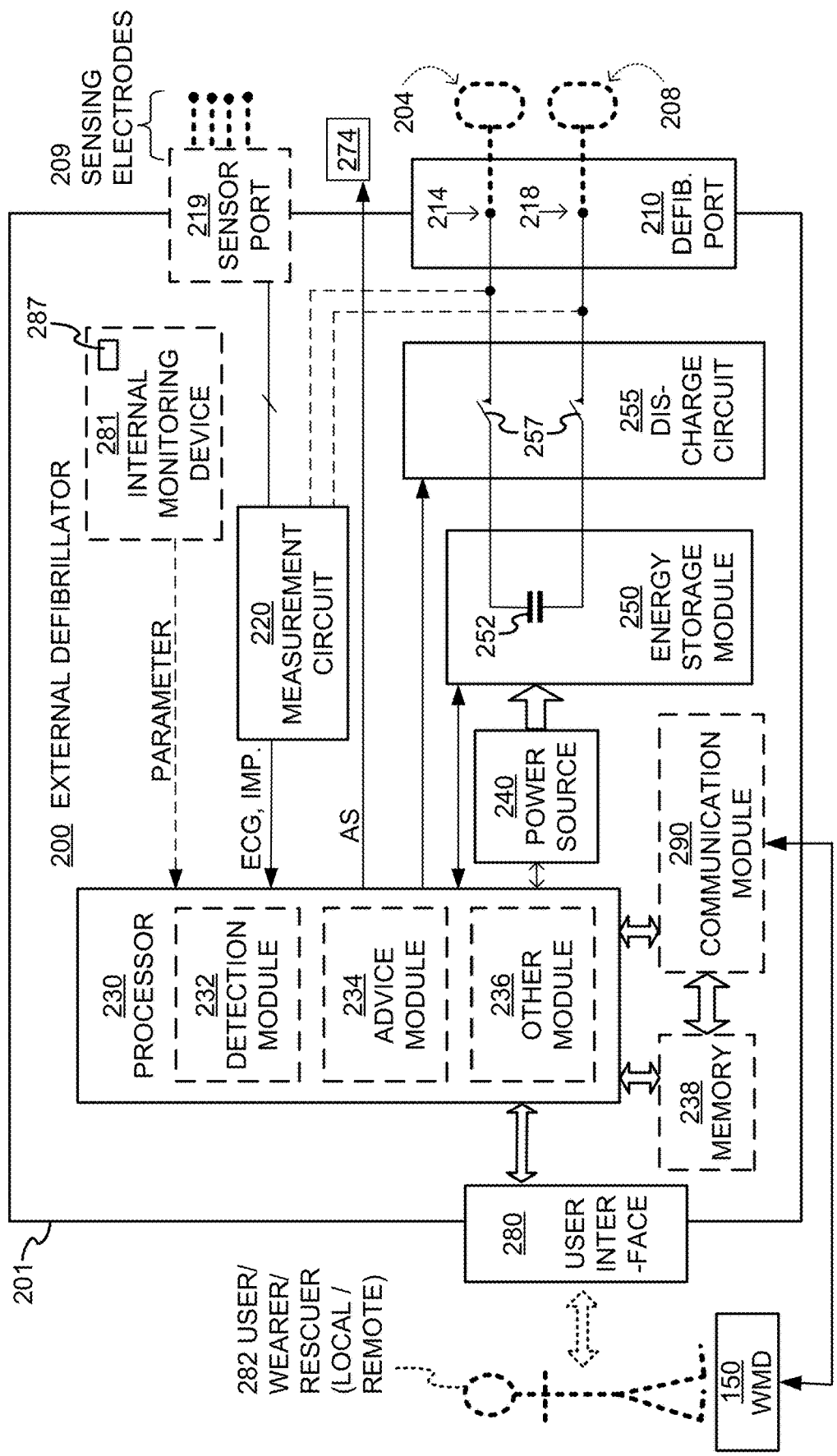
FIG. 2 is a time diagram showing sample components of an external defibrillator, such as the one belonging in the system of FIG. 1, and further showing a small form factor WMD in accordance with one or more embodiments.

FIG. 2 is a diagram showing sample components of an external defibrillator, such as the one belonging in the system 10 of FIG. 1, the system further including a small form factor WMD 150 in accordance with one or more embodiments. Some components of WCD system 10 can be, for example, included in external defibrillator 100 of FIG. 1. The components shown in FIG. 2 can be provided in a housing 201, which may also be referred to as casing 201.

As will be discussed in further detail, below, the components of WCD system 10 as shown in FIG. 2 can adaptively raise and lower the processing capability and/or performance of the WCD system 10 in response to a required workload or special needs. In one or more embodiments, one or more components of the WCD system 10 can alter their capability and/or performance on-the-fly while also providing significant power saving when operating at lower levels of performance and/or capability. Similarly, subsystems that can be partially or completely powered down when their capability is not needed can be used to reduce the power they spend. Using such techniques or methods, the components of the WMD system such as WCD system 10 can adapt to find an optimal, low-power operating point at any one time. Done repeatedly, the WMD system 10 can end up operating optimally for the bulk of its operation, while still being able to dynamically react to a situation, event, or development by bringing to bear other capabilities, temporarily increasing its power consumption.

External defibrillator 200 is intended for a patient who would be wearing it, such as ambulatory patient 82 of FIG. 1. Defibrillator 200 may further include a user interface 280 for a user 282. User 282 can be patient 82, also known as wearer 82. Alternatively, user 282 can be a local rescuer at the scene, such as a bystander who might offer assistance, or a trained person. Alternatively, user 282 might be a remotely located trained caregiver in communication with the WCD system 10.

User interface 280 can be made in a number of ways. User interface 280 may include output devices, which can be visual, audible or tactile, for communicating to a user 282 by outputting images, sounds or vibrations. Images, sounds, vibrations, and anything that can be perceived by user 282 can also be called human-perceptible indications (HPIs). There are many examples of output devices. For example, an output device can be a light, or a screen to display what is sensed, detected and/or measured, and provide visual feedback to user 282 acting as a rescuer for their resuscitation attempts, and so on. Another output device can be a speaker, which can be configured to issue voice prompts, beeps, loud alarm sounds and/or words to warn bystanders, etc.

User interface 280 further may include input devices for receiving inputs from users. Such input devices may include various controls, such as pushbuttons, keyboards, touchscreens, one or more microphones, and so on. An input device can be a cancel switch, which is sometimes called an "I am alive" switch or "live man" switch. In some embodiments, actuating the cancel switch can prevent the impending delivery of a shock and may be referred to as a stop button in such embodiments. In some examples, the input button can comprise a capacitive sensor input button.

Defibrillator 200 may include an internal monitoring device 281. Device 281 is called an "internal" device because it is incorporated within housing 201. Monitoring device 281 can sense or monitor patient parameters such as patient physiological parameters, system parameters and/or environmental parameters, all of which can be called patient data. In other words, internal monitoring device 281 can be complementary or an alternative to outside monitoring device 180 of FIG. 1. Allocating which of the parameters are to be monitored by which of monitoring devices 180, 281 can be done according to design considerations. Device 281 may include one or more sensors as also described elsewhere in this document.

Patient parameters may include patient physiological parameters. Patient physiological parameters may include, for example and without limitation, those physiological parameters that can be of any help in detecting by the WCD system 10 whether or not the patient is in need of a shock or other intervention or assistance. Patient physiological parameters may also optionally include the patient's medical history, event history, and so on. Examples of such parameters include the patient's ECG, blood oxygen level, blood flow, blood pressure, blood perfusion, pulsatile change in light transmission or reflection properties of perfused tissue, heart sounds, heart wall motion, breathing sounds and pulse. Accordingly, monitoring device 180 of FIG. 1 and/or monitoring device 281 of FIG. 2 may include one or more sensors configured to acquire patient physiological signals. Examples of such sensors or transducers include one or more electrodes to detect ECG data, a perfusion sensor, a pulse oximeter, a device for detecting blood flow (e.g. a Doppler device), a sensor for detecting blood pressure (e.g. a cuff), an optical sensor, illumination detectors and sensors perhaps working together with light sources for detecting color change in tissue, a motion sensor, a device that can detect heart wall movement, a sound sensor, a device with a microphone, an SpO2 sensor, and so on. In accordance with one or more embodiments, monitoring device 180 and/or monitoring device 281 can include a small form factor WMD 150, and the scope of the disclosed subject matter is not limited in this respect. In view of this disclosure, it will be appreciated that such sensors can help detect the patient's pulse, among other patient parameters, and can therefore also be called pulse detection sensors, pulse sensors, and pulse rate sensors. In addition, a person skilled in the art may implement other ways of performing pulse detection.

In some embodiments, the local parameter is a trend that can be detected in a monitored physiological parameter of patient 282. A trend can be detected by comparing values of parameters at different times over short and long terms. Parameters whose detected trends can particularly help a cardiac rehabilitation program include: a) cardiac function (e.g. ejection fraction, stroke volume, cardiac output, etc.); b) heart rate variability at rest or during exercise; c) heart rate profile during exercise and measurement of activity vigor, such as from the profile of an accelerometer signal and informed from adaptive rate pacemaker technology; d) heart rate trending; e) perfusion, such as from SpO2, CO2, or other parameters such as those mentioned above; f) respiratory function, respiratory rate, etc.; g) motion, level of activity; and so on. Once a trend is detected, it can be stored and/or reported via a communication link, optionally along with a warning if warranted. From the report, a physician monitoring the progress of patient (user) 282 will know about a condition that is either not improving or deteriorating.

Patient state parameters include recorded aspects of patient (user) 282, such as motion, posture, whether they have spoken recently plus may be also what they said, and so on, plus optionally the history of these parameters. Alternatively, one of these monitoring devices could include a location sensor such as a Global Positioning System (GPS) location sensor. Such a sensor can detect the location, plus a speed can be detected as a rate of change of location over time. Many motion detectors output a motion signal that is indicative of the motion of the detector, and thus of the patient's body. Patient state parameters can be very helpful in narrowing down the determination of whether sudden cardiac arrest (SCA) is indeed taking place.

A WCD system 10 made according to embodiments may thus include a motion detector 287. In embodiments, a motion detector can be implemented within monitoring device 180 or monitoring device 281. Such a motion detector can be made in many ways as is known in the art, for example by using an accelerometer. In this example, a motion detector 287 is implemented within monitoring device 281. A motion detector of a WCD system 10 according to embodiments can be configured to detect a motion event. A motion event can be defined as is convenient, for example a change in motion from a baseline motion or rest, etc. In such cases, a sensed patient parameter can include motion.

System parameters of a WCD system 10 can include system identification, battery status, system date and time, reports of self-testing, records of data entered, records of episodes and intervention, and so on. In response to the detected motion event, the motion detector may render or generate, from the detected motion event or motion, a motion detection input that can be received by a subsequent device or functionality.

Environmental parameters can include ambient temperature and pressure. Moreover, a humidity sensor may provide information as to whether or not it is likely raining. Presumed patient location could also be considered an environmental parameter. The patient location could be presumed or determined, if monitoring device 180 and/or monitoring device 281 includes a GPS location sensor as described above, and if it is presumed that the patient is wearing the WCD system 10.

Defibrillator 200 typically includes a defibrillation port 210, which can be a socket in housing 201. Defibrillation port 210 includes electrical node 214 and/or electrical node 218. Leads of defibrillation electrode 204 and/or defibrillation electrode 208, such as leads 105 of FIG. 1, can be plugged into defibrillation port 210 so as to make electrical contact with node 214 and node 218, respectively. It is also possible that defibrillation electrode 204 and/or defibrillation electrode 208 instead are connected continuously to defibrillation port 210. Either way, defibrillation port 210 can be used for guiding, via electrodes, to the wearer at least some of the electrical charge that has been stored in an energy storage module 250 that is described more fully later in this document. The electric charge will be the shock for defibrillation, pacing, and so on.

Defibrillator 200 may optionally also have a sensor port 219 in housing 201, which is also sometimes known as an ECG port. Sensor port 219 can be adapted for plugging in sensing electrodes 209, which are also known as ECG electrodes and ECG leads. It is also possible that sensing electrodes 209 can be connected continuously to sensor port 219, instead. Sensing electrodes 209 are types of transducers that can help sense an ECG signal, e.g. a 12-lead signal, or a signal from a different number of leads, especially if the leads make good electrical contact with the body of the patient and in particular with the skin of the patient. As with defibrillation electrodes 204 and/or 208, the support structure 170 can be configured to be worn by patient 282 so as to maintain sensing electrodes 209 on a body of patient (user) 282. For example, sensing electrodes 209 can be attached to the inside of support structure 170 for making good electrical contact with the patient, similarly with defibrillation electrodes 204 and/or 208.

Optionally a WCD system 10 according to embodiments also includes a fluid that can be deployed automatically between the electrodes and the patient's skin. The fluid can be conductive, such as by including an electrolyte, for establishing a better electrical contact between the electrodes and the skin. Electrically speaking, when the fluid is deployed, the electrical impedance between each electrode and the skin is reduced. Mechanically speaking, the fluid may be in the form of a low-viscosity gel so that it does not flow away after being deployed from the location it is released near the electrode. The fluid can be used for both defibrillation electrodes 204 and/or 208, and for sensing electrodes 209.

The fluid may be initially stored in a fluid reservoir, not shown in FIG. 2. Such a fluid reservoir can be coupled to the support structure 170. In addition, a WCD system 10 according to embodiments further includes a fluid deploying mechanism 274. Fluid deploying mechanism 274 can be configured to cause at least some of the fluid to be released from the reservoir and be deployed near one or both of the patient locations to which electrodes 204 and/or 208 are configured to be attached to the patient. In some embodiments, fluid deploying mechanism 274 is activated prior to the electrical discharge responsive to receiving activation signal (AS) from a processor 230, which is described more fully later in this document.

In some embodiments, defibrillator 200 also includes a measurement circuit 220, as one or more of its working together with its sensors or transducers. Measurement circuit 220 senses one or more electrical physiological signals of the patient from sensor port 219, if provided. Even if defibrillator 200 lacks sensor port 219, measurement circuit 220 optionally may obtain physiological signals through nodes 214 and/or 218 instead, when defibrillation electrodes 204 and/or 208 are attached to the patient. In these embodiments, the input reflects an ECG measurement. The patient parameter can be an ECG, which can be sensed as a voltage difference between electrodes 204 and 208. In addition, the patient parameter can be an impedance, which can be sensed between electrodes 204 and 208 and/or between the connections of sensor port 219 considered pairwise. Sensing the impedance can be useful for detecting, among other things, whether these electrodes 204 and/or 208 and/or sensing electrodes 209 are not making good electrical contact with the patient's body. These patient physiological signals may be sensed when available. Measurement circuit 220 can then render or generate information about them as inputs, data, other signals, etc. As such, measurement circuit 220 can be configured to render a patient input responsive to a patient parameter sensed by a sensor. In some embodiments, measurement circuit 220 can be configured to render a patient input, such as values of an ECG signal, responsive to the ECG signal sensed by sensing electrodes 209. More strictly speaking, the information rendered by measurement circuit 220 is output from it, but this information can be called an input because it is received as an input by a subsequent device or functionality.

Defibrillator 200 also includes a processor 230. Processor 230 may be implemented in a number of ways. Such ways include, by way of example and not of limitation, digital and/or analog processors such as microprocessors and Digital Signal Processors (DSPs), controllers such as microcontrollers, software running in a machine, programmable circuits such as Field Programmable Gate Arrays (FPGAs), Field-Programmable Analog Arrays (FPAAs), Programmable Logic Devices (PLDs), Application Specific Integrated Circuits (ASICs), a system on chip (SoC), any combination of one or more of these, and so on.

Processor 230 may include, or have access to, a non-transitory storage medium, such as memory 238 that is described more fully later in this document. Such a memory 238 can have a non-volatile component for storage of machine-readable and machine-executable instructions. A set of such instructions can also be called a program. The instructions, which may also be referred to as "software," generally provide functionality by performing acts, operations and/or methods as may be disclosed herein or understood by one skilled in the art in view of the disclosed embodiments. In some embodiments, and as a matter of convention used herein, instances of the software may be referred to as a "module" and by other similar terms. Generally, a module includes a set of the instructions to offer or fulfill a particular functionality. Embodiments of modules and the functionality delivered are not limited by the embodiments described in this document.

Processor 230 can be considered to have a number of modules. One such module can be a detection module 232. Detection module 232 can include a Ventricular Fibrillation (VF) detector. The patient's sensed ECG from measurement circuit 220, which can be available as inputs, data that reflect values, or values of other signals, may be used by the VF detector to determine whether the patient is experiencing VF. Detecting VF is useful because VF typically results in sudden cardiac arrest (SCA). Detection module 232 can also include a Ventricular Tachycardia (VT) detector, and so on.

Another such module in processor 230 can be an advice module 234, which generates advice for what to do. The advice can be based on outputs of detection module 232. There can be many types of advice according to embodiments. In some embodiments, the advice is a shock/no shock determination that processor 230 can make, for example via advice module 234. The shock/no shock determination can be made by executing a stored Shock Advisory Algorithm (SAA). A Shock Advisory Algorithm can make a shock/no shock determination from one or more ECG signals that are captured according to embodiments and determine whether or not a shock criterion is met. The determination can be made from a rhythm analysis of the captured ECG signal or otherwise.

In some embodiments, when the determination is to shock, an electrical charge is delivered to the patient. Delivering the electrical charge is also known as discharging and shocking the patient. As mentioned above, such can be for defibrillation, pacing, and so on.

In good or ideal conditions, a very reliable shock/no shock determination can be made from a segment of the sensed ECG signal of the patient. In practice, however, the ECG signal is often corrupted by electrical noise, which can make it difficult to analyze. Too much noise sometimes causes an incorrect detection of a heart arrhythmia, resulting in a false alarm to the patient. Noisy ECG signals may be handled as described in U.S. application Ser. No. 16/037,990, filed on Jul. 17, 2018 and since published as US 2019/0030351 A1, and in U.S. application Ser. No. 16/038,007, filed on Jul. 17, 2018 and since published as US 2019/0030352 A1, both by the same applicant and incorporated herein by reference in their entireties.

Processor 230 can include additional modules, such as other module 236, for other functions. In addition, if internal monitoring device 281 is provided, processor 230 may receive its inputs, etc.

Defibrillator 200 optionally further includes a memory 238, which can work together with processor 230. Memory 238 may be implemented in a number of ways. Such ways include, by way of example and not of limitation, volatile memories, Nonvolatile Memories (NVM), Read-Only Memories (ROM), Random Access Memories (RAM), magnetic disk storage media, optical storage media, smart cards, flash memory devices, any combination of these, and so on. Memory 238 is thus a non-transitory storage medium. Memory 238, if provided, can include programs and/or instructions for processor 230, which processor 230 may be able to read and execute. More particularly, the programs can include sets of instructions in the form of code, which processor 230 may be able to execute upon reading. Executing is performed by physical manipulations of physical quantities, and may result in functions, operations, processes, acts, actions and/or methods to be performed, and/or the processor to cause other devices or components or blocks to perform such functions, operations, processes, acts, actions and/or methods. The programs can be operational for the inherent needs of processor 230, and can also include protocols and ways that decisions can be made by advice module 234. In addition, memory 238 can store prompts for user 282, if this user is a local rescuer. Moreover, memory 238 can store data. This data can include patient data, system data and environmental data, for example as learned by internal monitoring device 281 and outside monitoring device 180. The data can be stored in memory 238 before it is transmitted out of defibrillator 200, or be stored there after it is received by defibrillator 200.

Defibrillator 200 can optionally include a communication module 290, for establishing one or more wired and/or wireless communication links with other devices of other entities, such as a remote assistance center, Emergency Medical Services (EMS), and so on. The communication module 290 may include short range wireless communication circuitry for example in accordance with a BLUETOOTH or ZIGBEE standard, short or medium range wireless communication for example a W-Fi or wireless local area network (WLAN) in accordance with an Institute of Electrical and Electronics Engineers (IEEE) 802.11x standard, or a wireless wide area network (WWAN) in accordance with a Third Generation Partnership Project (3GPP) including a 3G, 4G, or 5G New Radio (NR) standard. The communication links can be used to transfer data and commands. The data may be patient data, event information, therapy attempted, cardiopulmonary resuscitation (CPR) performance, system data, environmental data, and so on. For example, communication module 290 may transmit wirelessly, e.g. on a daily basis, heart rate, respiratory rate, and other vital signs data to a server accessible over the internet, for instance as described in U.S. application Ser. No. 13/959,894 filed Aug. 6, 2012 and published as US 2014/0043149 A1 and which is incorporated herein by reference in its entirety. This data can be analyzed directly by the patient's physician and can also be analyzed automatically by algorithms designed to detect a developing illness and then notify medical personnel via text, email, phone, etc. Module 290 may also include such interconnected sub-components as may be deemed necessary by a person skilled in the art, for example an antenna, portions of a processor, supporting electronics, outlet for a telephone or a network cable, etc. Furthermore, in accordance with one or more embodiments, the small form factor WMD 150 can couple with communication module 290 of defibrillator 200 via a wired or wireless communication link. In some embodiments, the small form factor WMD 150 can couple with defibrillator 200 via outside monitoring device 180 of FIG. 1 acting as an intermediate device, connector, bus, router, switch, or hub, and the scope of the disclosed subject matter is not limited in this respect.

Defibrillator 200 also may include a power source 240. To enable portability of defibrillator 200, power source 240 typically includes a battery. Such a battery typically can be implemented as a battery pack, which can be rechargeable or not. Sometimes a combination of rechargeable and non-rechargeable battery packs is provided. Other embodiments of power source 240 can include an alternating current (AC) power override, for where AC power will be available, an energy-storing capacitor or bank of capacitors, and so on. Appropriate components may be included to provide for charging or replacing power source 240. In some embodiments, power source 240 is controlled and/or monitored by processor 230.

Defibrillator 200 additionally may include an energy storage module 250. Energy storage module 250 can be coupled to the support structure 170 of the WCD system 10, for example either directly or via the electrodes and their leads. Module 250 is where some electrical energy can be stored temporarily in the form of an electrical charge when preparing it for discharge to administer a shock. In some embodiments, module 250 can be charged from power source 240 to the desired amount of energy as controlled by processor 230. In typical implementations, module 250 includes a capacitor 252 which can be a single capacitor or a system or bank of capacitors, and so on. In some embodiments, energy storage module 250 includes a device that exhibits high power density such as an ultracapacitor. As described above, capacitor 252 can store the energy in the form of an electrical charge for delivering to the patient.

A decision to shock can be made responsive to the shock criterion being met, as per the above-mentioned determination. When the decision is to shock, processor 230 can be configured to cause at least some or all of the electrical charge stored in module 250 to be discharged through patient 82 while the support structure is worn by patient 82 so as to deliver a shock 111 to patient 82.

For causing the discharge, defibrillator 200 can include a discharge circuit 255. When the decision is to shock, processor 230 can be configured to control discharge circuit 255 to discharge through the patient 82 at least some or all of the electrical charge stored in energy storage module 250. Discharging can be to nodes 214 and/or 218, and from there to defibrillation electrodes 204 and/or 208, so as to cause a shock to be delivered to the patient. Circuit 255 can include one or more switches 257. Switches 257 can be made in a number of ways, such as by an H-bridge, and so on. Circuit 255 could also be thus controlled via processor 230, and/or user interface 280.

A time waveform of the discharge may be controlled by thus controlling discharge circuit 255. The amount of energy of the discharge can be controlled by how much energy storage module has been charged, and by how long discharge circuit 255 is controlled to remain open. Defibrillator 200 optionally can include other components.

Figure 3:
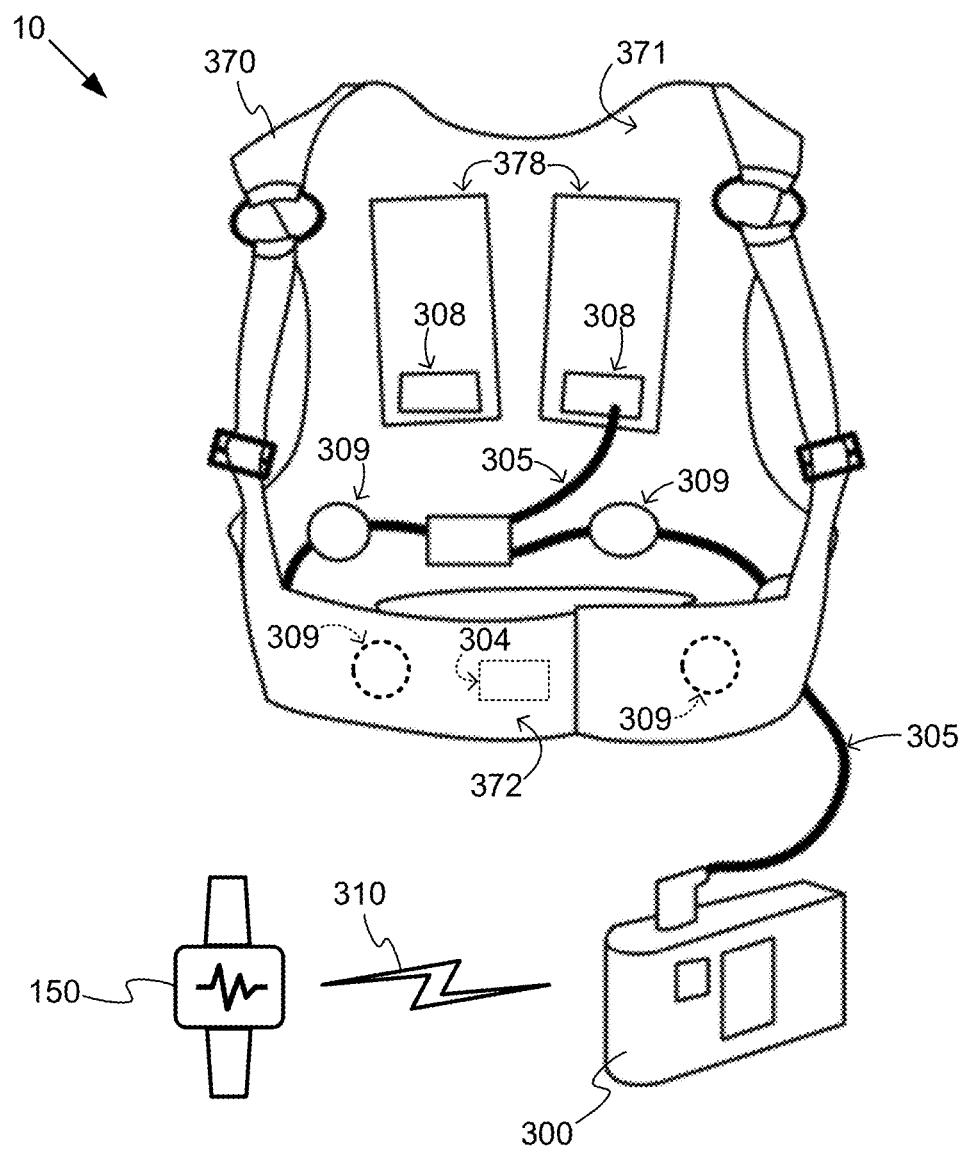
FIG. 3 is a diagram of sample embodiments of components of a WCD system and a small form factor WMD in accordance with one or more embodiments.

FIG. 3 is a diagram of sample embodiments of components of a WCD system and a small form factor WMD in accordance with one or more embodiments. A support structure 370 includes a vest-like wearable garment. Support structure 370 has a back side 371, and a front side 372 that closes in front of the chest of the patient.

The WCD system 10 of FIG. 3 also includes an external defibrillator 300. FIG. 3 does not show any support for external defibrillator 300, which may be carried in a purse, on a belt, by a strap over the shoulder, and so on. Wires 305 connect external defibrillator 300 to electrodes 304, 308, and/or 309. Of those, electrodes 304 and 308 are defibrillation electrodes, and electrodes 309 are ECG sensing electrodes.

Support structure 370 is configured to be worn by the ambulatory patient to maintain electrodes 304, 308, and/or 309 on a body of the patient. Back defibrillation electrodes 308 can be maintained in pockets 378. The inside of pockets 378 can be made with loose netting, so that electrodes 308 can contact the back of the patient 82, especially with the help of the conductive fluid that has been deployed in such embodiments. In addition, sensing electrodes 309 are maintained in positions that surround the patient's torso, for sensing ECG signals and/or the impedance of the patient 82.

ECG signals in a WCD system 10 may include too much electrical noise to be useful. To ameliorate the problem, multiple ECG sensing electrodes 309 are provided, for presenting many options to processor 230. These options are different vectors for sensing the ECG signal, as described in more detail below.

In accordance with one or more embodiments, the small form factor WMD 150 can communicate with external defibrillator 300, for example via a wireless communication link 310 in some embodiments. In other embodiments the small form factor WMD 150 also can communicate with external defibrillator 300 via a wired communication link, and the scope of the disclosed subject matter is not limited in this respect. An example of a small form factor WMD 150 is shown in and described with respect to FIG. 4, below.

Figure 4:
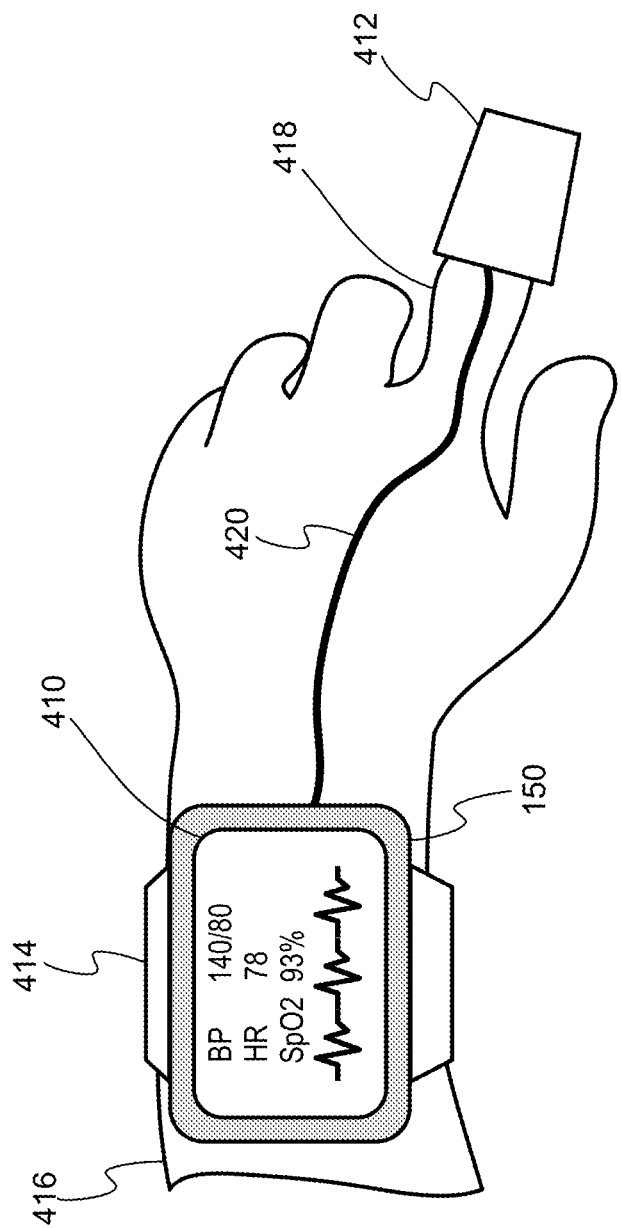
FIG. 4 is a diagram of an example small form factor WMD that is capable of operating independently or with a WCD in accordance with one or more embodiments.

FIG. 4 is a diagram of an example small form factor WMD that is capable of operating independently or with a WCD system in accordance with one or more embodiments. The embodiment of the small form factor WMD 150 as shown in FIG. 4 shows a wrist worn device that includes a display 410 to display blood pressure, heart rate, and/or SpO2 readings of the patient as some examples of patient parameters that can be obtained with or monitored by the small form factor WMD 150. In some examples, the small form factor WMD 150 can be attached to the patient's wrist 416 using a strap 414. In addition, an SpO2 and/or temperature sensor 412 may be attachable to a finger 418 of the patient 82 or may attach to the patient at any suitable location. A cable or wire 420 can be used to connect the SpO2 and/or temperature sensor 412 to the small form factor WMD 150 which can include circuitry to receive and process the signals from the SpO2 and/or temperature sensor 412. In some embodiments, the small form factor WMD 150 can include one or more sensors, processors, input/output circuits, and/or communication modules as discussed herein.

In one or more embodiments, the SpO2 sensor 412 is placed distant from the ECG sensing electrodes 209 and the defibrillation electrodes 204 and 208 of FIG. 2. For example, as shown in FIG. 4, the SpO2 sensor 412 is placed on a patient's finger and away from the other electrodes that are attached to the patient's torso. In particular embodiments, the SpO2 sensor 412 communicates with the WCD system 10 via wireless communication links, for example where the signals provided from the SpO2 sensor 412 to the small form factor WMD 150 is transmitted to the WCD system 10 via a wireless communication link 310 as shown in FIG. 3. In one or more embodiments, the small form factor WMD 150 comprises a cuff-less blood pressure device, and in other embodiments the small form factor WMD 150 can include a small blood pressure cuff located in or as part of the strap 414, and the scope of the disclosed subject matter is not limited in this respect. Furthermore, in one or more embodiments, the small form factor WMD 150 can be configured to utilize pulse transit time (PTT) to obtain continuous blood pressure monitoring, although the scope of the disclosed subject matter is not limited in this respect.

In one or more embodiments, the small form factor WMD 150 can be calibrated to enhance the accuracy of the measurements obtained. For example, the small form factor WMD 150 can be calibrated based on one or more external measurements obtained with one or more other devices. For example, the patient's blood pressure measurement may be obtained using a blood pressure cuff that can provide an electronic blood pressure reading to a smartphone via a wireless communication link. The readings obtained from one or more other devices then can be provided to the small form factor WMD 150, and that data can be used to help calibrate the small form factor WMD 150. The data obtained from the other devices can be provided to the small form factor WMD 150 via an electronic connection to the other devices such as BLUETOOTH, ZIGBEE, or Wi-Fi, or through manual entry such as entering the data via a user interface of the small form factor WMD 150, via the web, via an assistant, and so on. The small form factor WMD 150 can have the ability to monitor present and past activity of the patient 82 to determine the best times to collect an accurate patient parameter measurement. For example, the small form factor WMD 150 may decide to only take patient parameter measurements after the patient 82 has been inactive for at least five minutes, or at certain times of day. The small form factor WMD 150 also may assign a reliability score or weighting to measurements based on patient activity to facilitate the analysis of when blood pressure measurements should be obtained. In some embodiments, the small form factor WMD 150 can discriminate measurements obtained when the patient has changed from a sitting or lying down position to a standing position. WCD system 10 and/or the small form factor WMD 150 can include an accelerometer to detect when the patient 82 has changed positions and to measure the delta in patient parameter readings between two or more positions. Furthermore, such patient position based readings can also be used to determine a relative fitness or health measurement of the patient. In one or more embodiments, WCD system 10 can detect patient position and/or movement as described in U.S. application Ser. No. 16/205,861 filed Nov. 30, 2018 and which is incorporated herein by reference in its entirety. Once pertinent readings and measurements have been made, the data may be used to facilitate monitoring of the patient 82 by the WCD system 10 for an episode and/or to facilitate shock or no-shock decisions are shown in and described with respect to FIG. 6, below.

Figure 5:
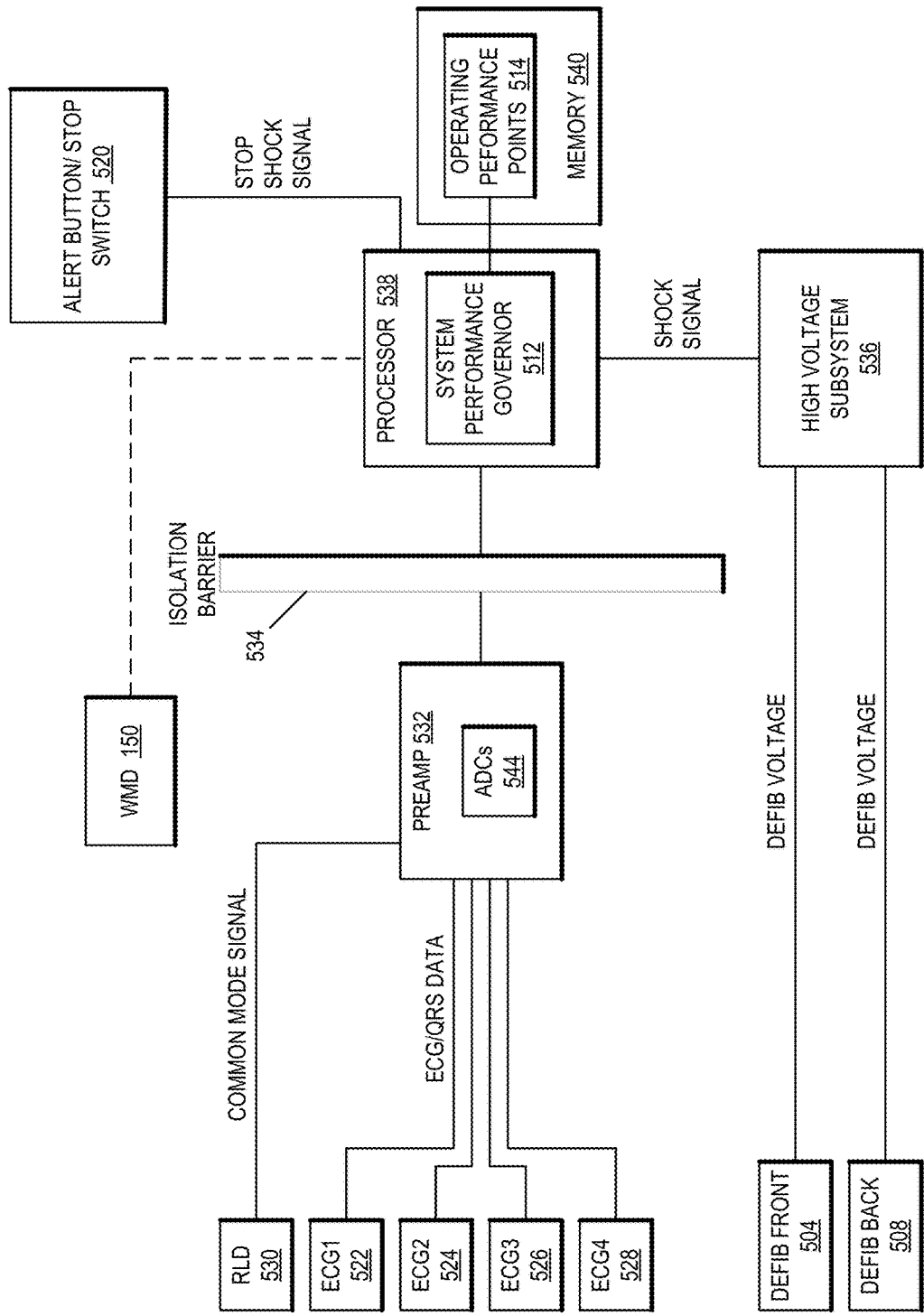
FIG. 5 is a diagram of a WCD system that can use a system performance governor to control power consumption in accordance with one or more embodiments.

FIG. 5 is a diagram of components of a wearable medical device that can use a system performance governor to control power consumption in accordance with one or more embodiments. The wearable medical device 500 of FIG. 5 can comprise a WCD system 10 that incorporates one or more of the features discussed herein to enhance ECG and QRS complex signal data detection along with heart rate data detection, and can optionally work with the small form factor 150 WMD. In one or more examples, the wearable medical device 500 of FIG. 5 can comprise a single device, one or more components, a system comprising one or more subsystems, a system comprising one or more devices, or a system that comprises one or more devices and/or one or more subsystems and/or one or more components, and the scope of the disclosed subject matter is not limited in these respects. Furthermore, a system can comprise a single device, a system can comprise one or more components, a system can comprise one or more subsystems, a system can comprise one or more devices, or a system can comprise one or more devices and/or one or more subsystems and/or one or more components, and the scope of the disclosed subject matter is not limited in these respects. In the example shown in FIG. 5, WMD 500 can include one or more components and/or one or more subsystems of a WDC system 10 as discussed herein and as shown in FIG. 1 and FIG. 3. Furthermore, the elements of WMD 500 of FIG. 5 can comprise or include one or more of the components of WCD system 10 as shown in and described with respect to FIG. 2. For example, the processor of 538 of FIG. 1 can be the same component or otherwise can be analogous to the processor 230 of FIG. 2, and so on, and the scope of the disclosed subject matter is not limited in this respect. In addition, WMD 500 optionally can include or otherwise can operate cooperatively with one or more small form factor wearable medical devices such as small form factor WMD 150, and the scope of the disclosed subject matter is not limited in this respect.

The ECG electrodes, ECG1 522, ECG2 524, ECG3 526, and ECG4 528 can be implemented in a number of ways. One such way is by using silver or silver plated copper electrodes that dry attach to the skin of the patient 82. The ECG electrodes provide ECG/QRS data to preamplifier 532. The preamplifier 532 may have a wide dynamic range at its input, for example+/−1.1 V which is much larger than the amplitude of the ECG signals which are about 1 mV. The preamplifier 532 includes analog-to-digital converters (ADCs) 544 to convert the ECG signals into a digital format. A right-leg drive (RLD) electrode 530 is used to provide a common mode signal so that the ECG signal from the ECG electrodes may be provided to preamplifier 532 as differential signals. The digital ECG signals are provided from the preamplifier 532 eventually to the main processor 538 via an optional isolation barrier 534. When provided, isolation barrier 534 operates to electrically isolate the preamplifier 532 and the ECG signals from the rest of the circuitry of WCD system 10.

The processor 538 processes the digital ECG/QRS data received from the preamplifier 532 with one or more digital filters. Since the preamplifier 532 has a wide dynamic range that is much wider than the amplitude range of the ECG signals, the digital filters can be utilized to process the ECG/QRS data without concern for clipping the incoming signals. One of the digital filters may include a matched filter to facilitate identification of QRS pulses in the incoming data stream. The wide dynamic range of the preamplifier 532 allows at least most of the ECG filtering to happen in software without the signal being clipped. The digital filters can be very effective at removing artifacts from the ECG/QRS data and may contribute to the enhanced false positive performance, that is a lower false positive rate, of the WCD system 10 according to embodiments as described herein.

The processor 538 can apply a rhythm analysis algorithm (RAA) using QRS width information and heart rate data extracted from the digital ECG data using the segment-based processing analysis 600 of FIG. 6 as describe below, and QRS width versus heart rate, to make a shock or no-shock determination. The RAA receives the digitized ECG signal and calculates the heart rate and QRS width for each segment. The digitized ECG signal is passed over the isolation barrier 534, and the heart rate is derived from the digitized ECG signal. The heart rate and QRS width are used for making a shock/no-shock decision for each segment, which then can lead to an alarm and a shock. In the event a shockable event is identified, the processor 538 will open a tachycardia episode to start the shock process. Unless the patient 82 provides a patient response using the alert button/stop switch 520 or other user interface of the WCD system 10 to send a stop shock signal to the processor 538 to intervene before the shock is applied, the processor 538 can send a shock signal to the high voltage subsystem 536 which will apply a defibrillation voltage across the defib front electrode 804 and the defib back electrode 508 to apply one or more therapeutic shocks until there is no longer any shockable event (VT or VF) or until the energy in the battery of the high voltage subsystem 536 is depleted.

In one or more embodiments of the WCD system 10, the digital filters coupled with the wide dynamic range of the preamplifier 532 may allow analysis of signals that otherwise would be clipped in systems with a more limited dynamic range. In addition, the matched filter of the digital filters preferentially highlights complexes similar to the patient's normal rhythm. As a result, artifacts that otherwise may be difficult to discriminate using other methods may be significantly attenuated by the matched filter.

In accordance with one or more embodiments, the small form factor WMD 150 can include an SpO2 and/or temperature sensor that can be coupled to the preamp 532. The small form factor WMD 150 can be coupled to the processor 538 via a wired link or a wireless communication link as discussed herein. In some embodiments, patient impedance measurements may be obtained between any two or more of the ECG electrodes, for example to determine a patient's respiration. In some embodiments, the wearable medical device (WMD) 500 can comprise a WCD system 10 as discussed herein. In other embodiments, the WMD 500 can comprise a wearable patient monitoring system that is capable of collecting one or more patient parameters that can be stored in a memory for future review and analysis, and/or to provide one or more warnings to a patient that one or more patient parameters are outside a normal or predetermined range when the patient is wearing the patient monitoring system, for example to allow the patient to cease a present activity that may be causing an atypical patient parameter or to otherwise seek assistance or medical help. In such embodiments, wearable system does not necessarily include structure to provide defibrillation therapy to the patient. It should be noted, however, that these are merely example implementations of WMD 500, and the scope of the disclosed subject matter is not limited in this respect.

In one or more embodiments, WMD 500, including WCD system 10, can involve one or more of the following features. Processor 538 can include a system performance governor 512 that can be embodied as hardware, software, and/or firmware, and which can select different profiles of one or more operating performance points (OPPs) 514 that can be stored in memory 540 for different system components based on the dynamic demands of the WMD 500 and the perceived needs of the ambulatory patient 82. Although FIG. 5 shows System Performance Governor 512 operating on processor 538, it should be noted that one or more other electronic and/or software elements of WMD 500, for example any one or more of the components of FIG. 2, can have the ability to dynamically switch among different OPPs 514 with different processing power and/or capability and associated power consumption. In some embodiments, memory 540 and OPPs 514 can be external to processor 538, and in other embodiments, memory 540 and OPPs 514 can be internal to processor 538. Various Operating Performance Points 514 can be thought of as monitoring states of different performance (high/low/mid), or different states of vigilance (high/med/low), among other examples. In some embodiments, certain system components can dynamically manage their OPPs 514 directly based on requests for their service without needing direction from the System Performance Governor 512. Examples of such components can include processors, microcontrollers, and/or communication modules such as BLUETOOTH, ZIGBEE, or Wi-Fi communication modules, although the scope of the disclosed subject matter is not limited in these respects.

In some embodiments, a number of electronic components and/or software packages may be used to dynamically switch among different operating performance points 514 because they that support adaptive, on-the-fly changes to performance and/or capability along with power savings at lower performance levels. In some examples, processor 538 can utilize Dynamic Voltage and Frequency Scaling (DVFS) as provided in application processors. DVFS capability allows a single-core or set of multi-core processors and their peripherals to support a broad range of processing power and power consumption profiles, on-the-fly, based on the needs of the application. This is typically accomplished by defining different Operating Performance Points 514 comprising combinations of supply voltage and/or frequency that processor 538 and/or one or more cores of processor 538 can switch among, on-the-fly. Since power consumption is directly proportional to operating frequency and proportional to the square of operating voltage, controlling frequency and power operating points can provide significant influence on power. For example, Table 1 below is an example OPP table for the Texas Instruments (TI) OMAP35x processor and which shows different OPPs for its ARM based applications processor, its digital signal processor (DSP), and its interconnect circuitry. In one or more embodiments, processor 538 can comprise a TI OMAP35x processor, and the following OPPs 514 can be stored in memory 540 to be accessed by System Performance Governor 538.

TABLE 1

Operating Performance Points for TI OMAP35x

|  | OPP | ARM MHZ | DSP MHZ | VDD1 | OPP | L3 MHz | VDD2 |
|---|---|---|---|---|---|---|---|
| OMAP 35xx | 5 | 650 | 430 | 1.35 | 3 | 166 | 1.15 |
|  | 4 | 550 | 400 | 1.27 | 2 | 100 | 1 |
|  | 3 | 500 | 360 | 1.2 | 1 | 41.5 | 0.95 |
|  | 2 | 250 | 180 | 1 |  |  |  |
|  | 1 | 125 | 90 | 0.95 |  |  |  |

In some embodiments, preamplifier 532 used for the ECG front end integrated circuits of WMD 500 can comprise an Analog Devices ADAS1000 that can be set to lower-performance configurations, for example fewer ECG acquisition channels and/or less ECG resolution, and higher-performance configurations, for example more ECG acquisition channels and higher ECG resolution, with corresponding power consumption benefits and/or penalties. For example, Table 2 below shows typical power consumption and performance differences for the Analog Devices ADAS1000 in "High Performance Mode" compared to "Low Power Mode".

TABLE 2

Power Consumption and Noise Performance for ADAS1000 Configurations

| POWER DISSIPATION Externally Supplied ADCVDD and DVDD[3] All 5 Input Channels and RLD | | | All 5 channels enabled, RLD enabled, pace enabled |
|---|---|---|---|
| | 27 | mW | High performance (low noise) |
| | 21 | mW | Low power mode |

Table 4. Typical Input Referred Noise (μV p-p)[1]

| Mode | Data Rate[2] | GAIN 0 (×1.4) +/− 1 VCM | GAIN 1 (×2.1) +/− 0.67 VCM | GAIN 2 (×2.8) +/− 0.5 VCM | GAIN 3 (×4.2) +/− 0.3 VCM |
|---|---|---|---|---|---|
| Analog Lead Mode[3] High Performance | | | | | |
| Mode | 2 kHz (0.5 Hz to 40 Hz) | 12 | 8.5 | 6 | 5 |
| | 2 kHz (0.5 Hz to 150 Hz) | 20 | 14.5 | 10 | 8.5 |
| | 2 kHz (0.05 Hz to 250 Hz) | 27 | 18 | 14.5 | 10.5 |
| | 2 kHz (0.05 Hz to 450 Hz) | 33.5 | 24 | 19 | 13.5 |
| | 16 kHz | 95 | 65 | 50 | 39 |
| | 128 kHz | 180 | 130 | 105 | 80 |
| Low Power Mode | 2 kHz (0.5 Hz to 40 Hz) | 13 | 9.5 | 7.5 | 5.5 |
| | 2 kHz (0.5 Hz to 150 Hz) | 22 | 15.5 | 12 | 9 |
| | 16 kHz | 110 | 75 | 59 | 45 |
| | 128 kHz | 215 | 145 | 116 | 85 |

In some embodiments, WMD 500 can include one or more BLUETOOTH hardware and/or software communication modules that support both low-power, lower-bandwidth Bluetooth Low Energy (BLE) and high-power, high-bandwidth/broad-capability Bluetooth Classic for communication between various components of WMD 500. For example, Table 3 below compares different performance metrics and power consumption figures for "Classic Bluetooth" and "Bluetooth Low Energy" OPPs 514.

TABLE 3

Bluetooth versus Bluetooth Low Energy Comparison

| Technical specification | Classic Bluetooth technology | Bluetooth low energy technology |
|---|---|---|
| Radio frequency | 2.4 GHz | 2.4 GHz |
| Distance/Range | ~10-100 meters | ~10-100 meters |
| Symbol rate | 1-3 Mbps | 1 Mbps |
| Application throughput | 0.7-2.1 Mbps | 305 kbps |
| Nodes/Active slaves | 7 | Unlimited |
| Security | 56 to 128 bit | 128 bit AES |
| Robustness | FHSS | FHSS |
| Latency (from not connected state to send data) | 100+ ms | <6 ms |
| Government regulation | Worldwide | Worldwide |
| Certification body | Bluetooth SIG | Bluetooth SIG |
| Voice capable | Yes | No |
| Network topology | Point-to-point, scatternet | Point-to-point, star |
| Power consumption | 1 (reference value) | 0.01 to 0.5 (use case dependent) |
| Service discover | Yes | Yes |
| Profile concept | Yes | Yes |
| Primary use cases | Mobile phones, headsets, stereo audio, automotive, PCs etc. | Mobile phones, gaming, PCs, sport & fitness, medical, automotive, industrial, automation, home electronics etc. |

In some examples, WMD system 500 comprises a WCD system 10 having a defibrillation therapy subsystem with the ability to perform high voltage charging, defibrillation shock delivery, impedance monitoring, and defibrillation electrode contact sensing functions that also can be completely powered off, with the exception of the electrode contact sensing, when the other functions are not needed. In such embodiments, System Performance Governor 512 can operate responsive to the dynamic needs of the WCD system 10. This responsiveness can be driven by automatic mechanisms such as operating system idle time monitoring or other scheduling algorithms that predict the need for more performance or less performance. The System Performance Governor 512 can also respond to direct requests for more performance or less performance and/or capability based on major states of the medical device. For purposes of example, segment based processing of an arrythmia event is shown in and described with respect to FIG. 6, below.

Figure 6:
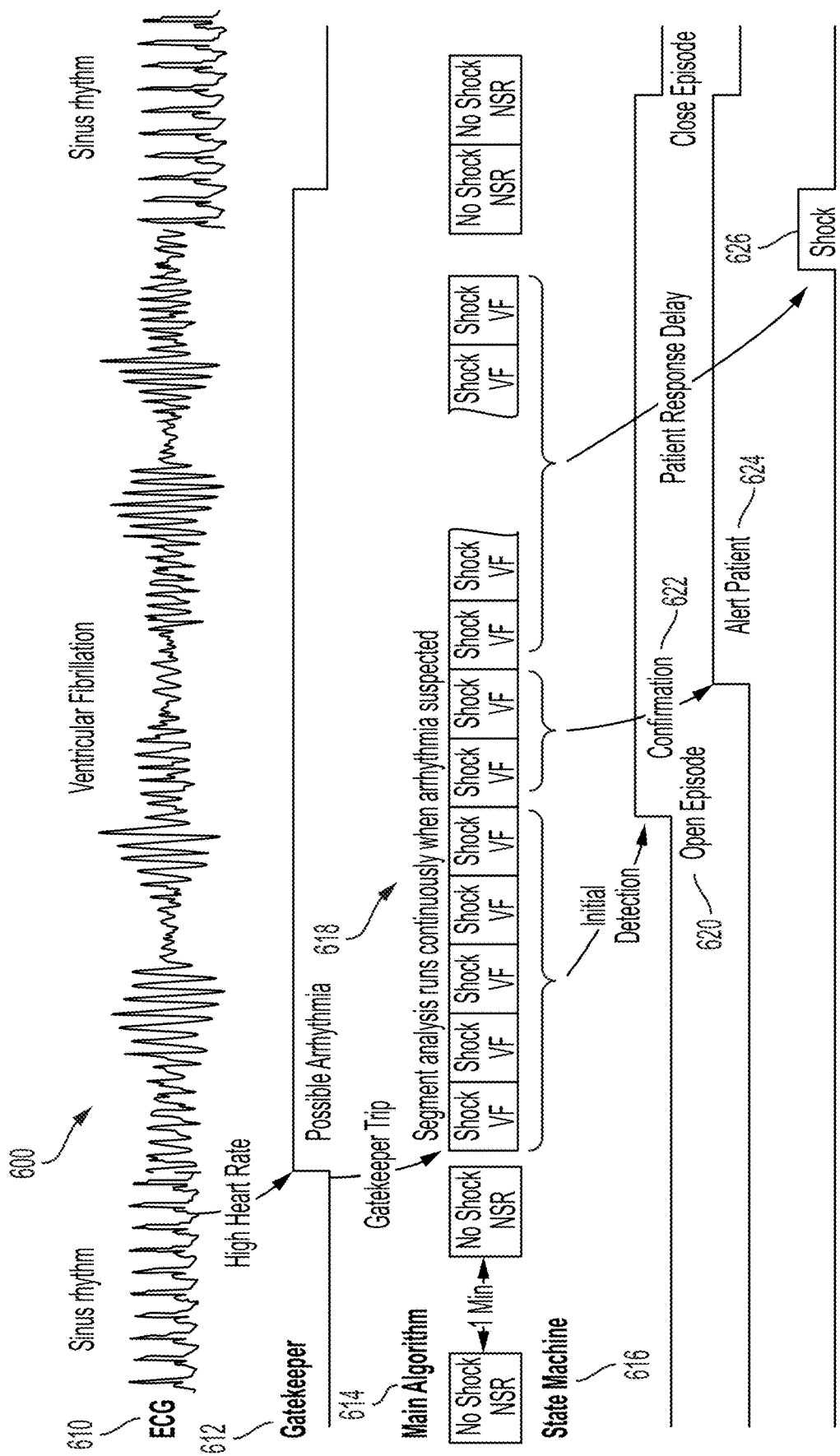
FIG. 6 is a diagram of segment based processing used in a WCD in accordance with one or more embodiments.

FIG. 6 is a diagram of segment based processing used in a WCD in accordance with one or more embodiments. The segment-based processing analysis 600 shown in FIG. 6 is utilized by WCD system 10 to make shock/no-shock decisions based at least in part on successive segments of ECG data. The segments can be 4.8 seconds in duration, although the scope of the disclosed subject matter is not limited in this respect.

The WCD system 10 monitors and analyzes ECG data 610 to make a shock/no-shock decision. A gatekeeper function 612 may be used to provide an early indication that an arrhythmia may be present in the patient 110. An example embodiment of this gatekeeper functionality is disclosed in U.S. application Ser. No. 15/715,500 filed Sep. 26, 2017 which is incorporated herein by reference in its entirety. In some embodiments, if an arrhythmia is suspected with the gatekeeper function 612, then the main rhythm analysis algorithm 614 is triggered to start analyzing successive segments 618 of ECG data, and a shock/no-shock decision is made for each of the individual segments 618. If a string of the segments 618, for example six segments, provide a shock decision, then an episode is opened (Open Episode) 620 in a state machine 616. In some embodiments, this starts an internal storage of ECG information in a memory of the WCD system 10 for later review. After the Open Episode 620, if the shockable rhythm persists for a confirmation period, for example for two or more segments for ventricular fibrillation (VF) or nineteen or more segments for ventricular tachycardia (VT) in some embodiments, then the patient alert sequence (Alert Patient) 624 is initiated. If the patient 82 does not respond within a specified amount of time after initiation of the patient alert sequence, for example after 20 seconds, then a shock (Shock) 626 is delivered to the patient 82.

In some embodiments, measurements from the small form factor WMD 150 can be captured and recorded as part of the episode data. In some cases, a blood pressure measurement obtained with the small form factor WMD 150 can open an episode if the measured blood pressure value is below or above predetermined minimum (Min) or maximum (Max) levels. The WCD system 10 can be configured to provide alerts to the patient 82 when measured blood pressure is below or above the predetermined Min/Max levels to provide, for example, a symptom report for example in which a patient can report whether he or she is exercising, experiencing dizziness, shortness of breath, vision problems, migraine, nose bleed, and so on. In some embodiments, the alert may prompt the patient to call 911, notify family members or a physician, check the small form factor WMD 150, and so on. In some embodiments, the alerts can be transmitted to remote parties such as clinicians and family members via the WCD system 10, via the small form factor WMD 150 itself, via a personal communication device such as smartphone, and/or via the remote data center or server such as "medical server". In some embodiments, the alert can be transmitted to the patient 82 via the personal communication device in addition to or instead of the WCD monitor component.

In some embodiments, the blood pressure measurement can be used in conjunction with, or as an input to, shock and/or pacing decision algorithms executed by the WCD system 10, for example where a low patient blood pressure can result from the patient being in VF or in bradycardia. In some embodiments, in addition to or instead of being used in therapy decision algorithms, the blood pressure measurement can be used to generate notifications and alerts related to an abnormal blood pressure, or in conjunction with the notifications and alerts provided by the therapy decision algorithms. In still other embodiments, additional sensors may be incorporated in the WCD system 10 to detect other patient parameters that may be used in the decision algorithm such as, for example, heart sound (audio) sensors, SpO2 sensors, Methemoglobin sensors, carbon monoxide sensors, carbon dioxide (CO2) sensors, temperature sensors, impedance, chemical sensors such as perspiration sensors, and so on. The data from these additional sensors optionally can be used in the decision algorithm in some embodiments and/or can be captured for post event or post episode review.

In some embodiments, alerts may be used to prompt the patient 82 to take a blood pressure measurement, for example by having the patient 82 obtain a reading with the small form factor WMD 150, to implement protocols in which the physician wants to track the patient's blood pressure. In some embodiments, the WCD system 10 can be configured to detect pulseless electrical activity (PEA) using the ECG and blood pressure measurements so that the WCD system 10 can alert one or more remote responders and/or prompt bystanders to perform cardiopulmonary resuscitation (CPR) on the patient 82. In some embodiments, blood pressure functionality can be used in providing CPR feedback in real-time or as part of a post event or post episode review. In some embodiments, data from multiple sensors can be aggregated to form vital sign data and provided to the patient, clinician, remote center, and so on. In still other embodiments, the small form factor WMD 150 and/or other sensors can provide vital sign monitoring but does not provide electrical therapy as part of the WCD system 10.

In some embodiments where the small form factor WMD 150 comprises an optical blood pressure sensor, the blood pressure measurement can be based on pulse transit time (PTT). In cuff-less blood pressure sensors based on PTT, the accuracy of the PTT measurements can be increased by incorporating the ECG data in the PTT calculation. In other embodiments, either alone or in combination, other patient signals such as impedance, respiration, acoustic, electromechanical, and/or imaging, can be used to enhance the PTT measurement.

In some embodiments, the blood pressure measurements, with or without other patient parameters such as heart rate, QRS width, SpO2, temperature, and so on, can be used to calculate a trend, a score, or figure of merit for the current cardiac state of the patient 82. This score can be transmitted to a remote receiver or device, to a doctor, a family member, a server, and so on, so that a bad trending data or score can alert the doctor or family member or other appropriate personnel to more closely monitor the patient 82, or even bring the patient 82 into a hospital or clinic.

Figure 7:
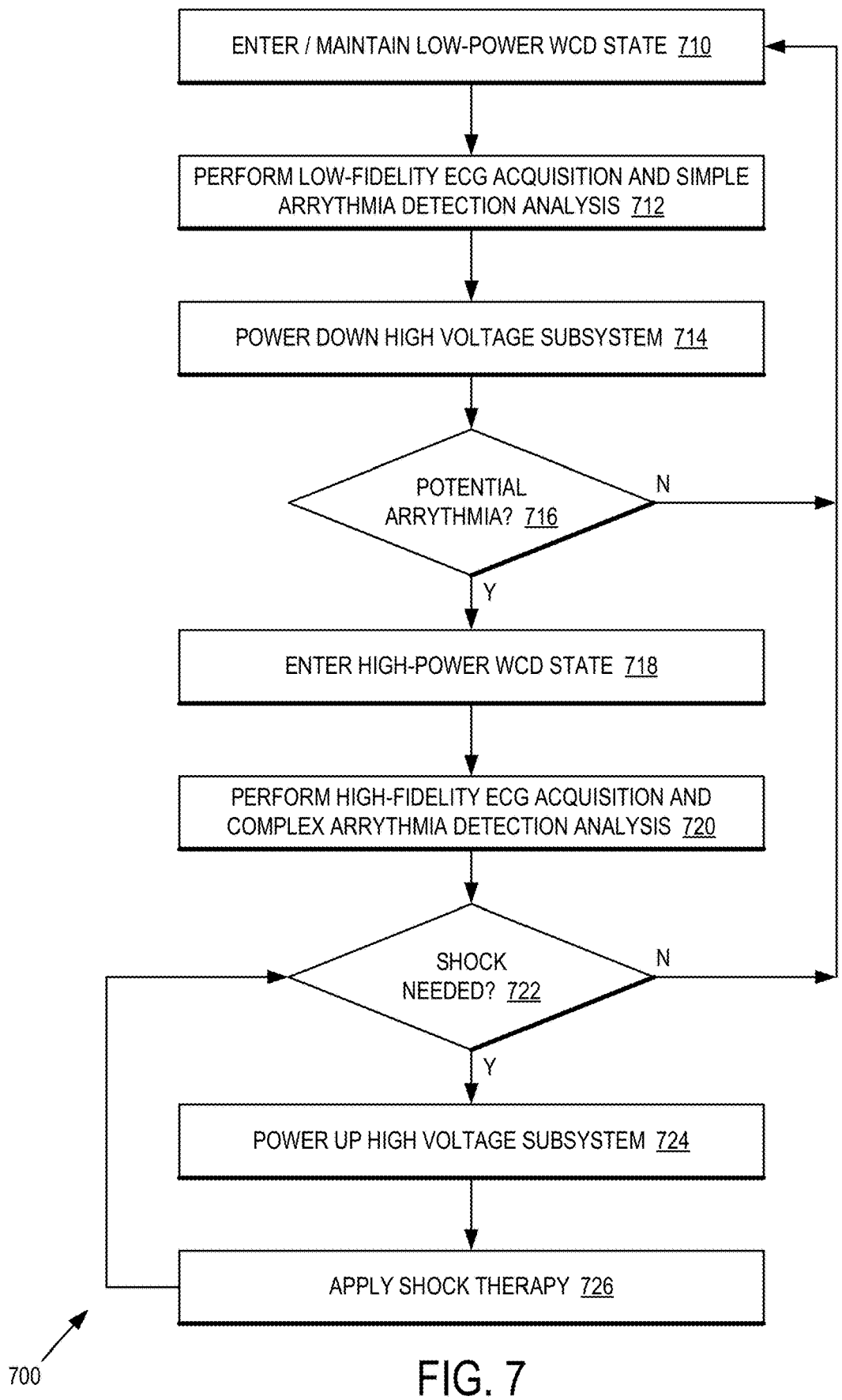
FIG. 7 is a diagram of a method to operate a WCD system at different power consumption states in accordance with one or more embodiments.

FIG. 7 is a diagram of a method to operate a WCD system at different power consumption states in accordance with one or more embodiments. In some examples, method 700 can be implemented by System Performance Governor 512 of FIG. 5. It should be noted that method 700 of FIG. 7 is merely one example of how WCD system 10 can be operated in different power consumption states, or using different Operating Performance Points, and method 700 can include more or fewer operations and/or different orders of the operations than shown in FIG. 7, and the scope of the disclosed subject matter is not limited in these respects. At operation 710, WCD system 10 can enter a low-power WCD state or can maintain the low-power state if already in the low-power state. For example, WCD system 10 may be operated to perform continuous, 24 hours a day, 7 days a week, ECG analysis of patient 82. System Performance Governor 512 can cause WCD system 10 to run most of the time in a low-power state and can cause WCD system 10 to perform at operation 712 using low-fidelity ECG acquisition and a simple, highly sensitive arrhythmia detection analysis algorithm. Furthermore, System Performance Governor 512 can cause high voltage subsystem 536 and all defibrillation therapy capability in the therapy subsystem to powered down at operation 714.

A determination can be made at decision block 716 whether or when a potential arrythmia is detected. If no potential arrytmia is detected, then method 700 may continue at operation 710 by maintaining the low-power state. If a potential arrhythmia is detected at decision block 716, WCD system 10 can enter a higher-power WCD state at operation 718. The WCD system 10 can perform a more sophisticated, computationally-complex arrhythmia detection analysis algorithm on high-fidelity/high-quality ECG data at operation 720. System Performance Governor 512 can increase the processing performance of specific computing elements and configure the ECG data collection system to its high performance mode. For example, processor 538 can be caused to operate at a higher voltage and/or at a higher operating frequency, and preamplifier 532 can analyze more channels of ECG data.

A determination can be made at decision block 722 whether and/or when a shock is needed to be delivered to the patient 82. In some embodiments, decision block 722 can implement the analysis shown in FIG. 6 and as described above. If no shock is needed as determined by the more complex arrythmia detection analysis using higher-fidelity ECG data, then System Performance Governor 512 can cause the WCD system 10 to enter the low-power state at operation 710. If a shockable rhythm is detected at decision block 722 as determined by the more complex arrythmia detection analysis using higher-fidelity ECG data, then the powered-down elements of the therapy subsystem such as the high voltage subsystem 536 can be powered up at operation 724 to enable charging, shock delivery, and impedance monitoring functions. One or more therapeutic shocks can be applied at operation 726 until a shock is no longer needed or until therapy energy of the high voltage subsystem 536 is depleted. When the arrhythmia is terminated by the defibrillation therapy and a normal rhythm is confirmed by the sophisticated algorithm, then the extended ECG acquisition, the sophisticated arrhythmia detection, and defibrillation therapy capabilities are no longer needed. When these capabilities are no longer needed, the System Performance Governor 512 can set the computing elements and ECG data collection system to enter the low-power WCD state at operation 710, operate at lower-power, lower-performance settings, and power down all functions of the therapy subsystem except for electrode contact sensing.

In one or more embodiments, certain power-adaptive components do not need the oversight and management of the System Performance Governor 512 to operate at different power states of at different Operating Performance Points 514. Instead, these power-adaptive components can dynamically increase or decrease their own Operating Performance Points 514 based on requests or demand for their use. For example, a combination BLUETOOTH and BLUETOOTH Low Energy (BLE) communication system can operate with BLE as the standard communication scheme. This provides low-power, low-bandwidth communication over a limited protocol like the Generic Attribute (GATT) profile. When higher-bandwidth communication and/or different communication protocols such as Serial Port Profile (SPP) or Personal Area Networking (PAN) are needed to communicate between system elements, a Classic Bluetooth connection can be made, and the higher performance communication link can be established. When the higher-performance communication link is no longer needed, the higher-power BLUETOOTH channel can be powered down.

In some embodiments, WCD system 10 can operate in a low-power, low-performance mode to prolong the life of the battery. One or more of the following functions can be implemented to operate in a low-power state. The number of channels or number of sensors being analyzed by the rhythm detection algorithm can be reduced. The length or repetitiveness of UI indication can be reduced. The WCD system 10 can have an ambient light sensor that allows the indicator light-emitting diodes (LEDs) and liquid crystal display (LCD) backlight LEDs to be set to the lowest needed operational current. One or more of the following strategies can be used in reaction to a detected arrhythmia. The operating performance point of the WCD system 10 can be maximized to speed up analysis of previously acquired data. The operating performance point of the system can be maximized to stabilize response of system to core functionality including high voltage (HV) energy charging and transfer, continuous arrhythmia analysis, and/or data storage and transfer to external clients, for example using BLUETOOTH. Strategies could be used in reaction to sensing of atypical power consumption can include turning off BLUETOOTH if excessive, atypical communications with an external client is sensed, and logging unusual behavior that is not consistent with an expected power profile, for example health checking.

In some embodiments, the WCD system 10 can rely on sensors other than ECG for sensing what the patient 82 is doing. For example, WCD system 10 can detect patient activity, especially where patient activity repeats and thus can be monitored by other sensors. Activity of sleep or even sitting and watching television can be discerned with motion sensors and confirmed with the time clock for time of day, evening, or night, plus potentially learning of patient's patterns of sitting and watching television or sleeping. When it is known that the patient 82 is stationary, all that needs to be monitored is breathing, perhaps with interruptions of ECG. Breathing can be monitored with a motion sensor, heart sounds sensor, and so on, or a blood pressure monitor, but in some embodiments, breathing is monitored with a sensor that will not wake up the sleeping ambulatory patient. During that time, a low-performance monitoring state can be entered. When the WCD system 10 receives information from a motion sensor indicating sudden movement or change of posture, a higher-performance monitoring state can be entered.

Providing a wearable medical device (WMD) such as a wearable cardio defibrillator (WCD) or a small form factor WMD capable of operating at two or more power levels as described herein can result in simplified hardware and/or software designs to achieve power savings. The disclosed devices and methods can involve fewer application-specific hardware designs using multiple processors with different purposes. Furthermore, software does not need to be partitioned to run in different operating environments and/or processors to accommodate the application-specific hardware designs. Because the system can automatically adapt based one or more patient parameters, software does not need to be designed around explicit decisions by the patient or operator to enter and leave lower-power modes or states. In addition, a broader ranges of medical device applications can be served by such adaptive elements. For example, a WMD as described herein can comprise a reduced power and reduced sized ECG monitor and/or ECG recorder that can operate computing elements and/or ECG acquisition elements in lower-performance modes to achieve low-power operation. In another example, a full-featured Wearable Cardio Defibrillator (WCD) can have sophisticated arrhythmia detection capability can operate in a low-power configuration for long durations to maximizes its operating time but can adaptively operate in a high-power configuration when additional processing power is warranted.

Other embodiments include combinations and sub-combinations of features described or shown in the drawings herein, including for example, embodiments that are equivalent to: providing or applying a feature in a different order than in a described embodiment, extracting an individual feature from one embodiment and inserting such feature into another embodiment; removing one or more features from an embodiment; or both removing one or more features from an embodiment and adding one or more features extracted from one or more other embodiments, while providing the advantages of the features incorporated in such combinations and sub-combinations. As used herein, feature or features can refer to the structures and/or functions of an apparatus, article of manufacture or system, and/or the operations, acts, or modalities of a method.

The following examples may be implemented in accordance with one or more embodiments. In example one, a wearable cardioverter defibrillator (WCD) comprises a plurality of electrocardiography (ECG) electrodes and a plurality of defibrillator electrodes to contact the patient's skin when the WCD is delivering therapy to the patient, a preamplifier coupled to the ECG electrodes to obtain ECG data from the patient, a processor to receive the ECG data from the preamplifier, and a high voltage subsystem to provide a defibrillation voltage to the patient through the plurality of defibrillator electrodes in response to a shock signal received from the processor, wherein in a first power mode of a range of power modes the preamplifier is configured to perform low-fidelity ECG acquisition and the processor is configured to perform simple arrythmia detection analysis, and in a second mode of the range of power modes the preamplifier is configured to perform high-fidelity ECG acquisition and the processor is configured to perform complex arrythmia detection analysis. In example two, the high voltage subsystem is powered down in the first power mode, and the high voltage subsystem is powered up in the second power mode. In example three, the processor is to select the second power mode when the simple arrythmia detection analysis detects a possible arrythmia. In example four, the processor is to otherwise select another power mode of the range of power modes. In example five, the high voltage subsystem is to provide the defibrillation voltage when the complex arrythmia detection analysis determines a shock should be applied to the patient. In example six, the processor is configured to operate at a lower voltage and/or a lower frequency in the first power mode, and to operate at a higher voltage and/or a higher frequency in the second power mode. In example seven, the WCD further comprises a wearable medical device to obtain a patient parameter provided to the processor, wherein the wearable medical device comprises a circuit to manage its own power level. In example eight, the WCD further comprises a memory coupled to the processor, wherein the memory has a plurality of operating performance points stored thereon to cause the processor to configure a power mode from the range of power modes for one or more components of the WCD based at least in part on whether the WCD is in the first power mode or the second power mode. In example nine, the processor is configured to select a power mode from the range of power modes of the WCD based on patient activity and/or a location of the patient. In example ten, the preamplifier uses fewer ECG channels, a lower gain level, and/or a lower data rate in the first power mode, and uses more ECG channels, a higher gain level, and/or a higher data rate in the second power mode. In example eleven, the WCD further comprises a display and an ambient light sensor, wherein the display is configured to operate at a selected power mode of the range of power modes in response to a level of ambient light detected by the ambient light sensor.

In example twelve, a method to adapt the operating power of an adjustable power wearable medical device (WMD) comprises receiving one or more patient parameters of a patient from a small form factor WMD, operating the adjustable power WMD in a first power mode of a range of power modes while the small form factor WMD is monitoring the one or more patient parameters, detecting a triggering event based on the one or more patient parameters received from the small form factor WMD, and operating the adjustable power WMD in a second power mode of the range of power modes in response to the triggering event. In example thirteen, the small form factor WMD is worn on a wrist, arm, leg, ankle, or chest or the patient. In example fourteen, at least one of the one or more patient parameters comprises heart rate, blood pressure, SpO2, breathing, movement, activity, and/or location. In example fifteen, the power adjustable WMD is to monitor the one or more patient parameters when operating in the second power mode. In example sixteen, the power adjustable WMD is to apply therapy to the patient when operating in the second power mode. In example seventeen, the small form factor WMD controls its operating power independent of the operating power of the adjustable power WMD.

In example eighteen, a wearable medical device (WMD) comprises at least one patient parameter sensor to sense at least one patient parameter of a patient, a processor to analyze the at least one patient parameter, wherein the processor is to select a first power mode of a range of power modes, or a second power mode of the range of power modes based on the at least one patient parameter, and a memory coupled with the processor. In example nineteen, the at least one patient parameter sensor senses the at least one patient parameter at a lower fidelity when the processor selects the first power mode and senses the at least one patient parameter at a higher fidelity when the processor selects the second power mode. In example twenty, lower fidelity comprises using fewer sensors, a lower gain level, and/or a lower data rate, and higher fidelity comprises using more sensors, a higher gain level, and/or a higher data rate. In example twenty-one, the processor is configured to analyze the at least one patient parameter using a simple algorithm when the first power mode is selected and is configured to analyze the at least one patient parameter using a complex algorithm when the second power mode is selected. In example twenty-two, the processor is configured to operate at a lower voltage and/or at a lower frequency when the first power mode is selected and is configured to operate at a higher voltage and/or at a higher frequency when the second power mode is selected. In example twenty-three, the memory stores two or more operating performance points for the at least one patient parameter sensor and/or the processor, wherein the processors is to select an operating performance point for the at least one patient parameter sensor and/or the processor based on the at least one patient parameter.

In example twenty-four, a wearable cardioverter defibrillator (WCD) comprises a plurality of electrocardiography (ECG) electrodes and a plurality of defibrillator electrodes to contact the patient's skin when the WCD is delivering therapy to the patient, a preamplifier coupled to the ECG electrodes to obtain ECG data from the patient, a processor to receive the ECG data from the preamplifier, a memory to store a plurality of operating performance points for one or more components of the WCD, and a high voltage subsystem to provide a defibrillation voltage to the patient through the plurality of defibrillator electrodes in response to a shock signal received from the processor, wherein the processor is configured to select one or more of the plurality of operating performance points to operate the one or more components of the WCD. In example twenty-five, the operating performance points configure one or more of the components of the WCD to operate at a lower power level. In example twenty-six, the operating performance points configure one or more components of the WCD to operate at a medium power level. In example twenty-seven, the operating performance points configure one or more components of the WCD to operate at a higher power level. In example twenty-eight, the operating performance points configure the preamplifier to operate at a power profile selected from a range of power profiles. In example twenty-nine, the operating performance points configure the processor to operate at a power profile selected from a range of power profiles. In example thirty, the operating performance points configure the high voltage subsystem to operate at a power profile selected from a range of power profiles. In example thirty-one, the WCD further comprises a display and an ambient light sensor, wherein the operating performance points configure the display to operate at a power profile selected from a range of power profiles in response to a level of ambient light detected by the ambient light sensor.

In example thirty-two, a method to adapt the operating power of an adjustable power wearable medical device (WMD) comprises monitoring one or more patient parameters of a patient, operating the adjustable power WMD in a first mode of a range of power modes while the WMD is monitoring the one or more patient parameters, detecting a triggering event based on the one or more patient parameters, and operating the adjustable power WMD in a second power mode of a range of power modes in response to the triggering event. In example thirty-three, the triggering event comprises one or more of the patient parameters having a value outside of a predetermined range of values. In example thirty-four, at least one of the one or more patient parameters comprises heart rate, blood pressure, SpO2, breathing, movement, activity, and/or location. In example thirty-five, the power adjustable WMD is to monitor the one or more patient parameters at a higher fidelity when operating in the second power mode. In example thirty-six, the power adjustable WMD is to apply therapy to the patient when operating in the second power mode.

In example thirty-seven, a method to adapt the operating power of an adjustable power wearable medical device (WMD) comprises receiving one or more parameters from a non-medical device, operating the adjustable power WMD in a first power mode of a range of power modes while the non-medical device is monitoring the one or more parameters, detecting a triggering event based on the one or more parameters received from the non-medical device, and operating the adjustable power WMD in a second power mode of the range of power modes in response to the triggering event. In example thirty-eight, the parameters comprise one or more patient parameters and/or one or more non-medical parameters. In example thirty-nine, the triggering event comprises one or more of the parameters having a value outside of a predetermined range of values. In example forty, at least one of the parameters comprises heart rate, blood pressure, SpO2, breathing, movement, activity, and/or location. In example forty-one, the power adjustable WMD is to monitor the one or more parameters at a higher fidelity when operating in the second power mode. In example forty-two, the power adjustable WMD is to apply therapy to the patient when operating in the second power mode.

Although the claimed subject matter has been described with a certain degree of particularity, it should be recognized that elements thereof may be altered by persons skilled in the art without departing from the spirit and/or scope of claimed subject matter. It is believed that the subject matter pertaining to wearable cardioverter defibrillator with a non-invasive blood pressure monitor and many of its attendant utilities will be understood by the foregoing description, and it will be apparent that various changes may be made in the form, construction and/or arrangement of the components thereof without departing from the scope and/or spirit of the claimed subject matter or without sacrificing all of its material advantages, the form herein before described being merely an explanatory embodiment thereof, and/or further without providing substantial change thereto. It is the intention of the claims to encompass and/or include such changes.

What is claimed is:

1. A wearable medical device to monitor a heart rhythm of a patient, comprising:
   a support structure to be worn by the patient;
   a plurality of electrocardiography (ECG) electrodes coupled to the support structure and arranged to contact the patient's skin when the patient is wearing the support structure; and
   a processor configured with:
      a first mode to perform a first arrhythmia detection analysis using ECG data of one or more ECG channels derived from output signals of the plurality of ECG electrodes; and
      a second mode to perform a second arrhythmia detection analysis using ECG data of two or more ECG channels derived from output signals of the plurality of ECG electrodes;
      wherein performing the first arrhythmia detection analysis dissipates less power than performing the second arrhythmia detection analysis; and
      wherein the ECG data is sensed at a lower fidelity in the first mode, and the ECG data is sensed at a higher fidelity in the second mode, wherein the lower fidelity comprises using fewer of the ECG channels, a lower gain level, and a lower data rate for continuous ECG analysis, and the higher fidelity comprises using more of the ECG channels, a higher gain level, and a higher data rate for complex ECG analysis.

2. The wearable medical device of claim 1, wherein the processor comprises a plurality of processing devices.

3. The wearable medical device of claim 1, wherein the first arrhythmia detection analysis is used by the processor to determine whether the ECG data is indicative of a possible arrhythmia.

4. The wearable medical device of claim 3, wherein the processor is configured to perform the second arrhythmia detection analysis responsive to a determination that the ECG data is indicative of the possible arrhythmia.

5. The wearable medical device of claim 4, wherein the second arrhythmia detection analysis comprises determining whether the ECG data is indicative of a shockable event.

6. The wearable medical device of claim 1, wherein:
the first arrhythmia detection analysis comprises determining one or more patient physiological parameters using the ECG data and the second arrhythmia detection analysis determines one or more patient physiological parameters using the ECG data; and
a number of patient physiological parameters of the first arrhythmia detection analysis is less than a number of patient physiological parameters of the second arrhythmia detection analysis.

7. The wearable medical device of claim 6, wherein:
the first arrhythmia detection analysis comprises determining the patient's heart rate; and
the second arrhythmia detection analysis comprises determining the patient's heart rate and another physiological parameter using the ECG data.

8. The wearable medical device of claim 7, wherein:
the first arrhythmia detection analysis comprises determining the patient's heart rate using a single ECG channel of the ECG data; and
the second arrhythmia detection analysis comprises determining the patient's heart rate and QRS width using two or more ECG channels of the ECG data.

9. The wearable medical device of claim 1, wherein the processor comprises a preamplifier circuit coupled to the plurality of ECG electrodes.

10. The wearable medical device of claim 1, wherein the wearable medical device comprises a wearable cardioverter defibrillator.

11. A method to monitor a heart rhythm of a patient using a wearable medical device, the method comprising:
receiving, by the wearable medical device, electrocardiogram (ECG) data of a plurality of ECG channels derived from output signals of a plurality of ECG electrodes coupled to the patient;
performing, by the wearable medical device, a first arrhythmia detection analysis using the ECG data; and
performing, by the wearable medical device, a second arrhythmia detection analysis using the ECG data;
wherein the wearable medical device dissipates less power performing the first arrhythmia detection analysis than performing the second arrhythmia detection analysis; and
wherein the ECG data is sensed at a lower fidelity for the first arrhythmia detection analysis, and the ECG data is sensed at a higher fidelity for the second arrhythmia detection analysis, wherein the lower fidelity comprises using fewer of the ECG channels, a lower gain level, and a lower data rate for continuous ECG analysis, and the higher fidelity comprises using more of the ECG channels, a higher gain level, and a higher data rate for complex ECG analysis.

12. The method of claim 11, wherein the first arrhythmia detection analysis is used to determine whether the ECG data is indicative of a possible arrhythmia.

13. The method of claim 12, further comprising performing the second arrhythmia detection analysis responsive to a determination that the ECG data is indicative of the possible arrhythmia.

14. The method of claim 11, wherein the second arrhythmia detection analysis comprises determining whether the ECG data is indicative of a shockable event.

15. The method of claim 14, further comprising initiating therapy in response to a determination that the ECG data is indicative of the shockable event.

16. The method of claim 11, wherein:
the first arrhythmia detection analysis comprises determining one or more patient physiological parameters using the ECG data and the second arrhythmia detection analysis determines one or more patient physiological parameters using the ECG data; and
a number of patient physiological parameters of the first arrhythmia detection analysis is less than a number of patient physiological parameters of the second arrhythmia detection analysis.

17. The method of claim 16, wherein:
the first arrhythmia detection analysis comprises determining the patient's heart rate; and
the second arrhythmia detection analysis comprises determining the patient's heart rate and another physiological parameter using the ECG data.

18. The method of claim 17, wherein:
the first arrhythmia detection analysis comprises determining the patient's heart rate using a single ECG channel of the ECG data; and
the second arrhythmia detection analysis comprises determining the patient's heart rate and QRS width using two or more ECG channels of the ECG data.

19. The method of claim 11, wherein one ECG channel is used in the first arrhythmia detection analysis and four ECG channels are used in the second arrhythmia detection analysis.

20. The method of claim 11, wherein the wearable medical device comprises a wearable cardioverter defibrillator.

* * * * *